(12) United States Patent
Kishi

(10) Patent No.: US 9,492,236 B2
(45) Date of Patent: Nov. 15, 2016

(54) MEDICAL MANIPULATOR

(71) Applicant: OLYMPUS CORPORATION, Tokyo (JP)

(72) Inventor: Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 122 days.

(21) Appl. No.: 14/256,008

(22) Filed: Apr. 18, 2014

(65) Prior Publication Data

US 2014/0228861 A1 Aug. 14, 2014

Related U.S. Application Data

(63) Continuation of application No. PCT/JP2012/078084, filed on Oct. 24, 2012.

(30) Foreign Application Priority Data

Oct. 25, 2011 (JP) ................ 2011-233974

(51) Int. Cl.
*A61B 19/00* (2006.01)
*A61B 17/00* (2006.01)

(52) U.S. Cl.
CPC ........... *A61B 19/2203* (2013.01); *A61B 34/30* (2016.02); *A61B 34/37* (2016.02); *A61B 2017/00477* (2013.01)

(58) Field of Classification Search
CPC .............. A61B 19/2203; A61B 19/59; A61B 2019/2203; A61B 2019/2211; A61B 2019/2215; A61B 2019/2219; A61B 2019/2223; A61B 2019/2234; A61B 2019/223; A61B 2019/562; A61B 34/25; A61B 34/30; A61B 34/35; A61B 34/37; A61B 34/252; A61B 2034/301; A61B 2034/302; A61B 2034/303
See application file for complete search history.

(56) References Cited

U.S. PATENT DOCUMENTS 5,855,583 A 1/1999 Wang et al.
6,371,963 B1 4/2002 Nishtala et al.
(Continued)

FOREIGN PATENT DOCUMENTS

CN 101574272 A 11/2009
JP 2000-210295 A 8/2000
(Continued)

OTHER PUBLICATIONS

Chinese Office Action dated Oct. 10, 2015 from related Chinese Patent Application No. 201280049592.5, together with an English language translation.
(Continued)

*Primary Examiner* — Jonathan Miles
*Assistant Examiner* — Kankindi Rwego
(74) *Attorney, Agent, or Firm* — Scully, Scott, Murphy & Presser, P.C.

(57) ABSTRACT

A medical manipulator includes: a surgical instrument unit having an effector; and a surgical instrument drive unit provided detachably with respect to the surgical instrument unit. The surgical instrument drive unit includes: a pair of input members configured to advance and retract in opposite directions to each other; and a driving source configured to advance and retract the pair of input members. The surgical instrument unit includes: a first transmission member configured to move in the same direction as one of the pair of input members; a second transmission member configured to move in the same direction as another of the pair of input members; and a first inversion interlocking member engaged with the first transmission member and the second transmission member.

20 Claims, 15 Drawing Sheets

(56) References Cited

U.S. PATENT DOCUMENTS

| | | |
|---|---|---|
| 6,497,651 B1 | 12/2002 | Kan et al. |
| 2002/0082617 A1 | 6/2002 | Nishtala et al. |
| 2003/0191516 A1 | 10/2003 | Weldon et al. |
| 2006/0052664 A1 | 3/2006 | Julian et al. |
| 2006/0229666 A1 | 10/2006 | Suzuki et al. |
| 2009/0012365 A1 | 1/2009 | Ueno et al. |
| 2009/0209946 A1 | 8/2009 | Swayze et al. |
| 2011/0284614 A1 | 11/2011 | Farascioni |

FOREIGN PATENT DOCUMENTS

| | | |
|---|---|---|
| JP | 2000-262527 A | 9/2000 |
| JP | 2001-277157 A | 10/2001 |
| JP | 2004-122286 A | 4/2004 |
| JP | 2005-507679 A | 3/2005 |
| JP | 2005-521514 A | 7/2005 |
| JP | 3686947 B2 | 8/2005 |
| JP | 2007-029167 A | 2/2007 |
| JP | 2009-018027 A | 1/2009 |
| JP | 2009-189830 A | 8/2009 |
| WO | 97/18927 A1 | 5/1997 |
| WO | WO 03/001987 A2 | 1/2003 |
| WO | 03/084439 A1 | 10/2003 |

OTHER PUBLICATIONS

International Search Report dated Dec. 25, 2012 issued in PCT/JP2012/078084.

Extended Supplementary European Search Report dated Jul. 1, 2015 from related European Application No. 12 84 2716.8.

MEDICAL MANIPULATOR

This application is a continuation application based on a PCT Patent Application No. PCT/JP2012/078084, filed Oct. 24, 2012, whose priority is claimed on Japanese Patent Application No. 2011-233974, filed Oct. 25, 2011. The contents of both the PCT Application and the Japanese Application are incorporated herein by reference.

BACKGROUND OF THE INVENTION

Field of the Invention
The present invention relates to a medical manipulator.
Description of Related Art
In a related art, a medical manipulator for supporting a surgical operation is known.

In such a medical manipulator, a surgical instrument unit and a surgical instrument drive unit should be detachably provided to perform sterilization treatment with respect to the surgical instrument unit.

For example, in Japanese Patent No. 3686947, as such a medical manipulator, an active forceps in which a forceps distal end body structure and a forceps shaft section, which are included in a surgical instrument unit, are detachably provided at a forceps base section, which is included in a surgical instrument drive unit, is disclosed.

In the active forceps disclosed in Japanese Patent No. 3686947, in order to mount the surgical instrument unit, the forceps shaft section is inserted into a frame of the forceps base section, the forceps shaft section is rotated 60 degrees about a central axis of the frame to lock a locking member to a holder, and then a fastening screw of the clamp is fastened to fix the forceps shaft section to the frame.

SUMMARY OF THE INVENTION

According to a first aspect of the present invention, a medical manipulator includes: a surgical instrument unit having an effector configured to manipulate a target object; and a surgical instrument drive unit provided detachably with respect to the surgical instrument unit and configured to supply a driving force for driving the effector. The surgical instrument drive unit includes: a pair of input members disposed at one end of the surgical instrument drive unit in an attachment and detachment direction to the surgical instrument unit and configured to advance and retract in opposite directions to each other, and configured to transmit the driving force in an advance direction upon advance toward the surgical instrument unit; and a driving source configured to advance and retract the pair of input members. The surgical instrument unit includes: a first transmission member opposite to one of the pair of input members and supported so as to advance and retract in one end of the surgical instrument unit in the attachment and detachment direction to the surgical instrument drive unit, configured to receive the driving force by the one of the pair of input members and move in the same direction as the one of the pair of input members, and connected to the effector in the other end of the surgical instrument unit in the attachment and detachment direction; a second transmission member opposite to the other of the pair of input members and supported so as to advance and retract in the one end of the surgical instrument unit in the attachment and detachment direction to the surgical instrument drive unit, and configured to receive the driving force by the other of the pair of input members and move in the same direction as the other of the pair of input members; and a first inversion interlocking member engaged with the first transmission member and the second transmission member, and configured to transmit a moving amount of one of the first transmission member and the second transmission member to the other of the first transmission member and the second transmission member while inverting a moving direction.

According to a second aspect of the present invention, in the medical manipulator according to the first aspect of the present invention, the one of the pair of input members may be configured to advance and retract by being connected to the driving source. The surgical instrument drive unit may further include a second inversion interlocking member provided between the pair of input members, engaged with the pair of input members, and configured to transmit a moving amount of the one of the pair of input members to the other of the pair of input members while inverting the moving direction.

According to a third aspect of the present invention, in the medical manipulator according to the first aspect or the second aspect of the present invention, the pair of input members, the first transmission member, the second transmission member, and the first inversion interlocking member may be provided in a plurality of sets. In each of the plurality of sets, the one of the pair of input members may be disposed closer to a center of an end of the surgical instrument drive unit in the attachment and detachment direction than the other of the pair of input members.

According to a fourth aspect of the present invention, the medical manipulator according to any one of the first aspect to the third aspect of the present invention may further include an intermediate member provided between the surgical instrument unit and the surgical instrument drive unit and detachably connected to the surgical instrument unit and the surgical instrument drive unit. The intermediate member may include: a surgical instrument unit side end detachably connected to the one end of the surgical instrument unit; a drive unit side end detachably connected to the one end of the surgical instrument drive unit; a first intermediate transmission member opposite to and abutting the first transmission member and the one of the pair of input members; a second intermediate transmission member opposite to and abutting the second transmission member and the other of the pair of input members; a first guide section into which the first transmission member, the one of the pair of input members, and the first intermediate transmission member are inserted so as to advance and retract, the first guide section being configured to guide the first intermediate transmission member so as to advance and retract; and a second guide section into which the second transmission member, the other of the pair of input members, and the second intermediate transmission member are inserted so as to advance and retract, the second guide section being configured to guide the second intermediate transmission member so as to advance and retract.

According to a fifth aspect of the present invention, in the medical manipulator according to any one of the first aspect to the fourth aspect of the present invention, the surgical instrument unit may further include a biasing unit of surgical instrument unit configured to bias the first inversion interlocking member toward the one end of the surgical instrument unit in the attachment and detachment direction to the surgical instrument drive unit.

According to a sixth aspect of the present invention, in the medical manipulator according to the second aspect of the present invention, the surgical instrument drive unit may further include a biasing unit of drive unit configured to bias the second inversion interlocking member toward the one end of the surgical instrument drive unit in the attachment and detachment direction to the surgical instrument unit.

According to a seventh aspect of the present invention, in the medical manipulator according to any one of the first aspect to the sixth aspect of the present invention, the second transmission member may include a manipulation member protruding from the surgical instrument unit in a direction intersecting the attachment and detachment direction of the surgical instrument unit.

DETAILED DESCRIPTION OF THE INVENTION

Figure 1:
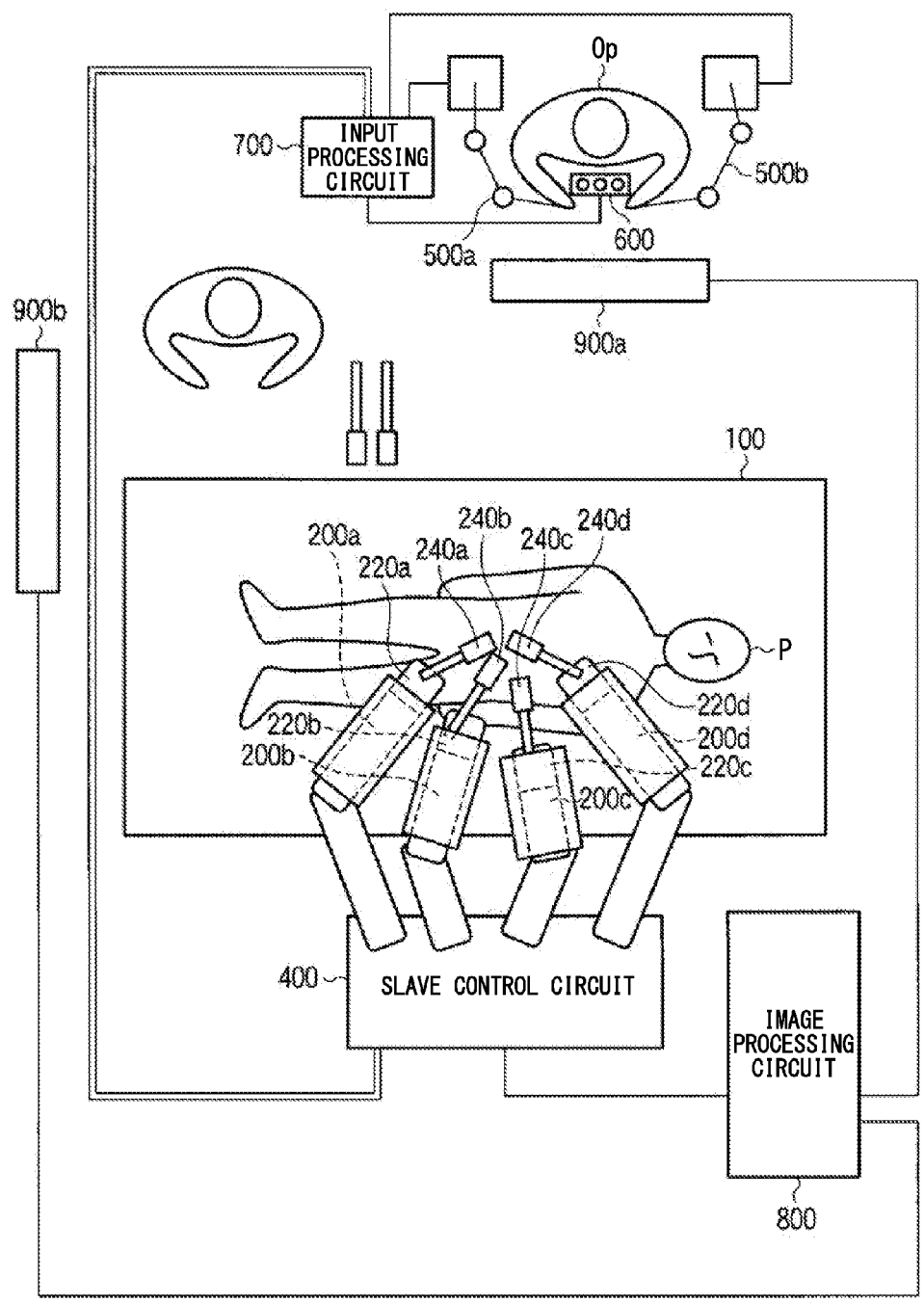
FIG. 1 is a schematic view showing an example of a configuration of a medical manipulator system, to which a medical manipulator according to an embodiment of the present invention is applied.

Hereinafter, embodiments of the present invention will be described with reference to the accompanying drawings. In all of the drawings, even when the embodiments are different from each other, the same or corresponding members are denoted by the same reference numerals, and common description thereof will be omitted.

(First Embodiment)

Hereinafter, a first embodiment of the present invention will be described. First, an example of a medical manipulator system, to which a medical manipulator according to the embodiment is applied, will be described.

FIG. 1 is a schematic view showing an example of a configuration of the medical manipulator system, to which the medical manipulator according to the embodiment is applied.

FIG. 1 shows an example of a master-slave type medical manipulator system employing. The master-slave type medical manipulator system is a system having two kinds of arms constituted by a master arm and a slave arm, and remotely controls the slave arm so as to follow an action of the master arm. As a configuration in which the surgical instrument is mounted on the slave arm, the medical manipulator according to the embodiment can be applied.

The medical manipulator system shown in FIG. 1 includes an operating table 100, slave arms 200a, 200b, 200c, and 200d, a slave control circuit 400, master arms 500a and 500b, a manipulation unit 600, an input processing circuit 700, an image processing circuit 800, a display 900a for an operator, and a display 900b for an assistant.

Hereinafter, for the purpose of brief description, reference numerals "Xa, Xb . . . , Xz" in alphabetical order may be represented as "Xa to Xz." For example, the slave arms 200a, 200b, 200c, and 200d may be represented as the slave arms 200a to 200d.

The operating table 100 is a table on which a patient P is placed as a subject to be observed and treated. The plurality of slave arms 200a to 200d are installed near the operating table 100. In addition, the slave arms 200a to 200d may be installed at the operating table 100.

Each of the slave arms 200a to 200d is configured to include a joint having multiple degrees of freedom. As the joint having multiple degrees of freedom is curved, positioning of a surgical instrument or the like mounted on a distal end side (a side directed to a body cavity of a patient P) of the slave arms 200a to 200d to the patient P placed on the operating table 100 is performed. The joint having multiple degrees of freedom is separately driven by a power unit (not shown). As the power unit, for example, a motor (a servomotor) having a servomechanism including an incremental encoder, a decelerator, or the like can be used. Action control of the power unit is performed by the slave control circuit 400.

The slave arms 200a to 200d include a plurality of power units (not shown) configured to drive surgical instruments 240a to 240d mounted thereon. As the power unit, for example, a servomotor can be used. Action control of the power unit is performed by the slave control circuit 400.

When the power units of the slave arms 200a to 200d are driven, a driving amount of the power unit is detected by a position detector. A detection signal from the position detector is input to the slave control circuit 400. By the detection signal, the driving amount of the slave arms 200a to 200d is detected in the slave control circuit 400.

Operation power transmission adaptors (hereinafter, simply referred to as "an adapter") 220a, 220b, 220c, and 220d are interposed between the slave arms 200a to 200d and the surgical instruments 240a to 240d to be connected to the slave arms 200a to 200d and the surgical instruments 240a to 240d, respectively. The adaptors 220a to 220d include drive mechanism configured to drive the surgical instruments 240a to 240d, respectively, and are configured to transmit power generated from the power unit of the corresponding slave arm to the corresponding surgical instrument.

For example, linear motion mechanisms, turning motion mechanisms, or the like, in accordance with a configuration of the corresponding surgical instrument, are installed at the drive mechanisms of the adaptors 220a to 220d.

The slave control circuit 400 is configured to include, for example, a CPU, a memory, or the like. The slave control circuit 400 stores a predetermined program configured to control the slave arms 200a to 200d, and controls actions of the slave arms 200a to 200d or the surgical instruments 240a to 240d in accordance with a control signal from the input processing circuit 700. That is, the slave control circuit 400 specifies a slave arm (or a surgical instrument) of a target object of the master arm manipulated by an operator Op based on the control signal from the input processing circuit 700, and calculates a driving amount required to apply movement of the operator Op in accordance with the manipulation amount of the master arm to the specified slave arm or the like.

Then, the slave control circuit 400 controls an action of the slave arm of the target object of the master arm or the like in accordance with the calculated driving amount. Here, the slave control circuit 400 inputs a driving signal into the corresponding slave arm, and controls a magnitude or a polarity of the driving signal such that the driving amount of the slave arm of the target object reaches a target driving amount in accordance with the detection signal input from the position detector of the power unit in accordance with the action of the corresponding slave arm.

The master arms 500a and 500b are constituted by a plurality of link mechanisms. For example, the position detector such as an incremental encoder or the like is installed at each link constituting the link mechanism. As the action of each link is detected by the position detector, the manipulation amount of the master arms 500a and 500b is detected in the input processing circuit 700.

The medical manipulator system of FIG. 1 is a system configured to manipulate four slave arms using the two master arms 500a and 500b. In the medical manipulator system of FIG. 1, there is a necessity to appropriately switch the slave arm of the target object of the master arm. For example, such switching is performed by manipulation of the manipulation unit 600 of the operator Op. Of course, when the number of master arms is equal to the number of slave arms to correspond to the target object one-to-one, such switching is not necessary.

The manipulation unit 600 includes various kinds of manipulation members such as a switch button configured to switch the slave arm of the target object of the master arms 500a and 500b, a scaling change switch configured to change an action ratio between the master and the slave, a foot switch configured to emergently stop the system, or the like. When any one of the manipulation members constituting the manipulation unit 600 is manipulated by the operator Op, the manipulation signal in accordance with the manipulation of the corresponding manipulation member is input from the manipulation unit 600 into the input processing circuit 700.

The input processing circuit 700 analyzes the manipulation signal from the master arms 500a and 500b and the manipulation signal from the manipulation unit 600, and generates a control signal for controlling the medical manipulator system in accordance with the analyzed result of the manipulation signal to input the control signal into the slave control circuit 400.

The image processing circuit 800 performs various kinds of image processing to display an image signal input from the slave control circuit 400, and generates image data for display in the display 900a for the operator and the display 900b for the assistant. The display 900a for the operator and the display 900b for the assistant are constituted by, for example, a liquid crystal display, and display an image based on the image data generated in the image processing circuit 800 in accordance with the image signal obtained via an observation instrument.

In the medical manipulator system configured as described above, when the operator Op manipulates the master arms 500a and 500b, the corresponding slave arm and the surgical instrument attached to the slave arm are operated in accordance with movement of the master arms 500a and 500b. Accordingly, a desired surgical operation on the patient P can be performed.

Next, the medical manipulator according to the present embodiment will be described.

Figure 2:
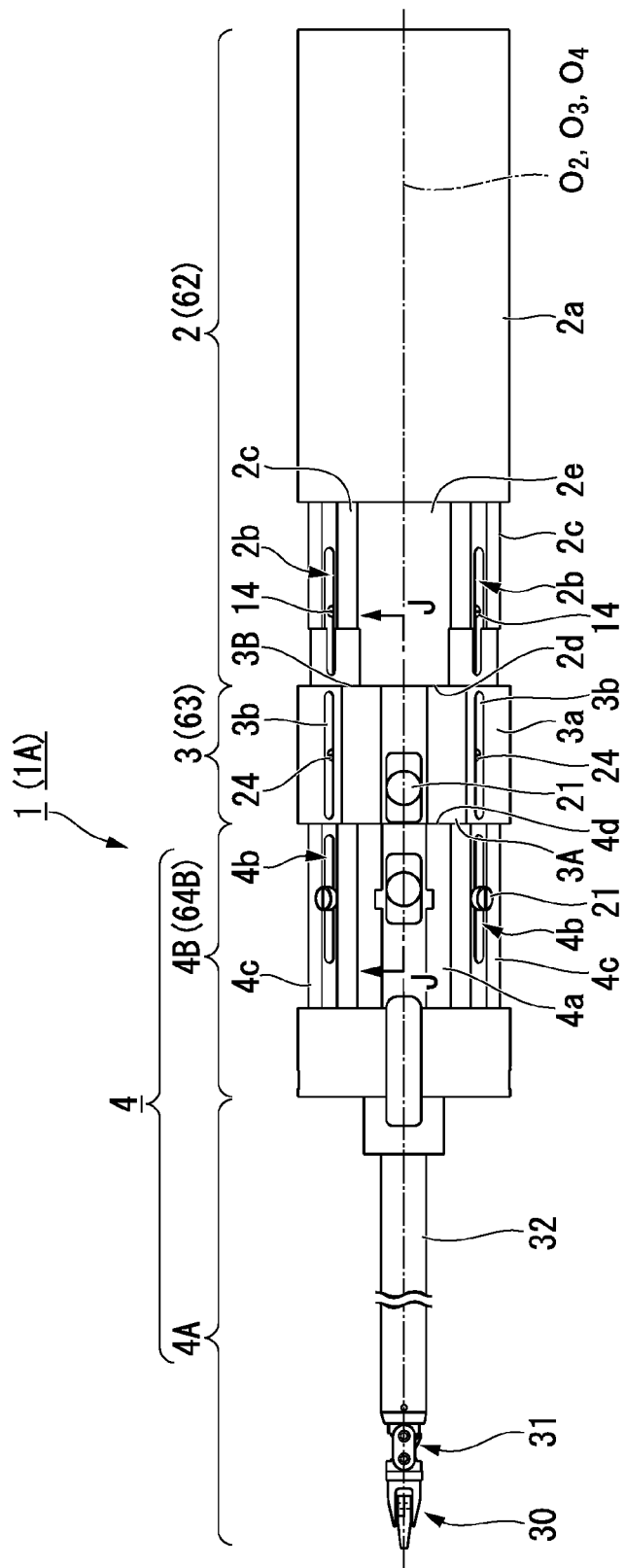
FIG. 2 is a schematic plan view showing a configuration of a medical manipulator according to a first embodiment of the present invention.
Figure 3:
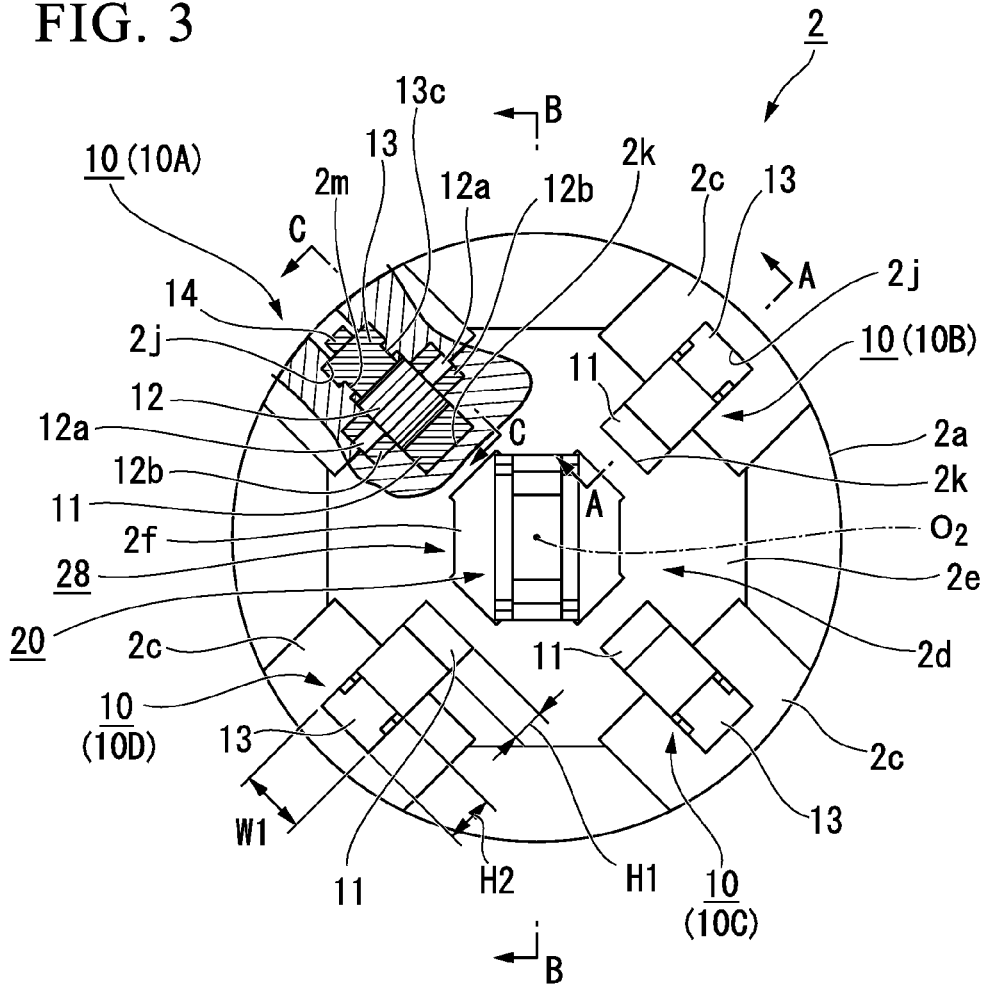
FIG. 3 is a schematic side view of a distal end side of a surgical instrument drive unit of the medical manipulator according to the first embodiment of the present invention.
Figure 4:
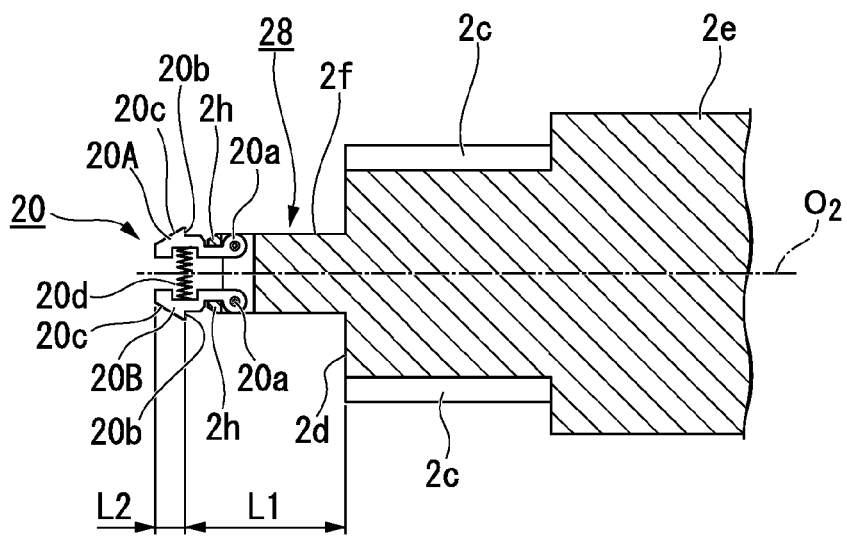
FIG. 4 is a cross-sectional view taken along line B-B of FIG. 3.
Figure 5:
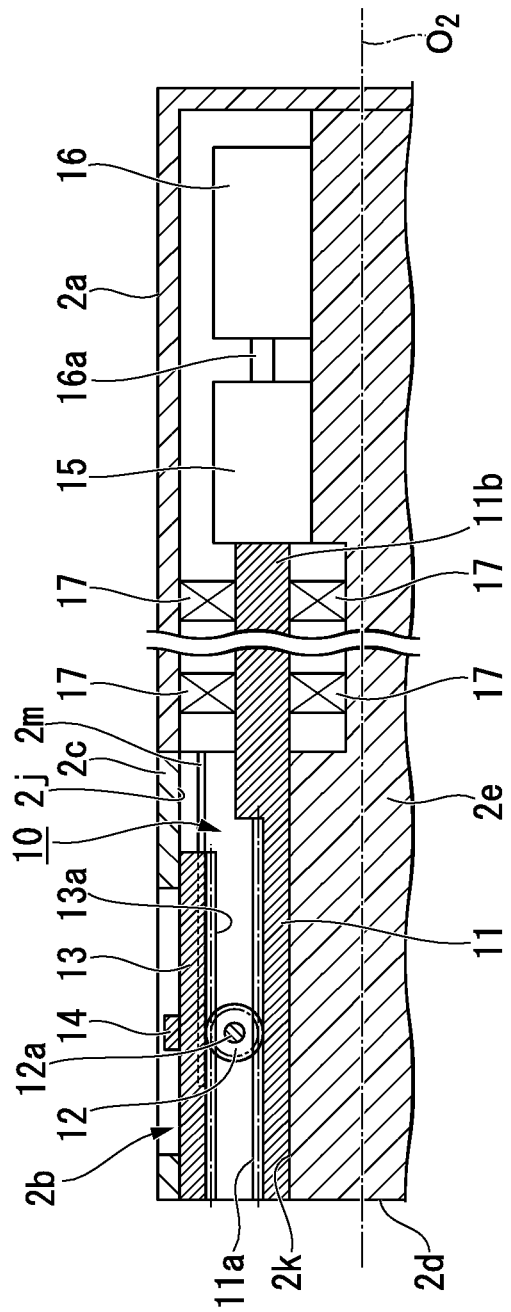
FIG. 5 is a cross-sectional view taken along line A-A of FIG. 3.
Figure 6:
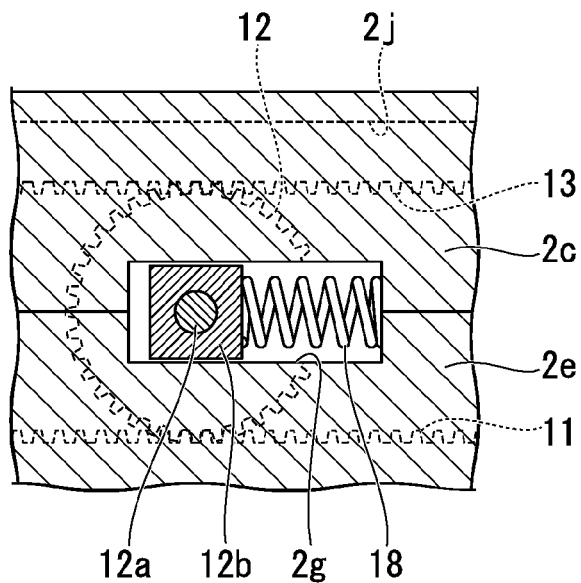
FIG. 6 is a cross-sectional view taken along line C-C of FIG. 3.
Figure 7:
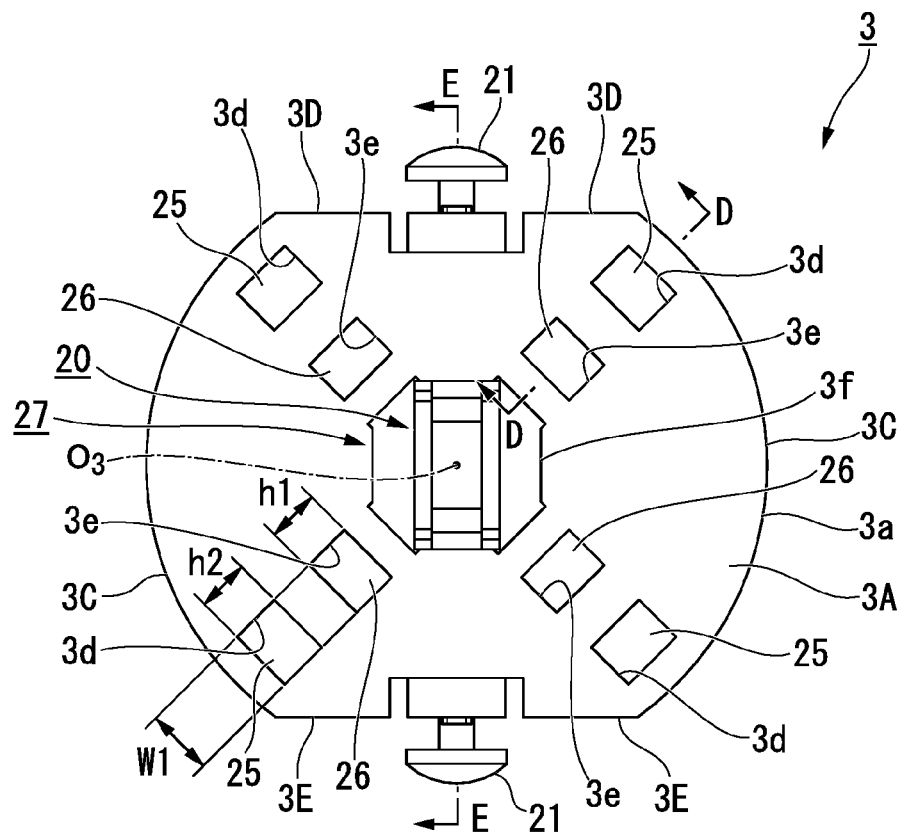
FIG. 7 is a schematic side view of a distal end side of an intermediate member of the medical manipulator according to the first embodiment of the present invention.
Figure 8:
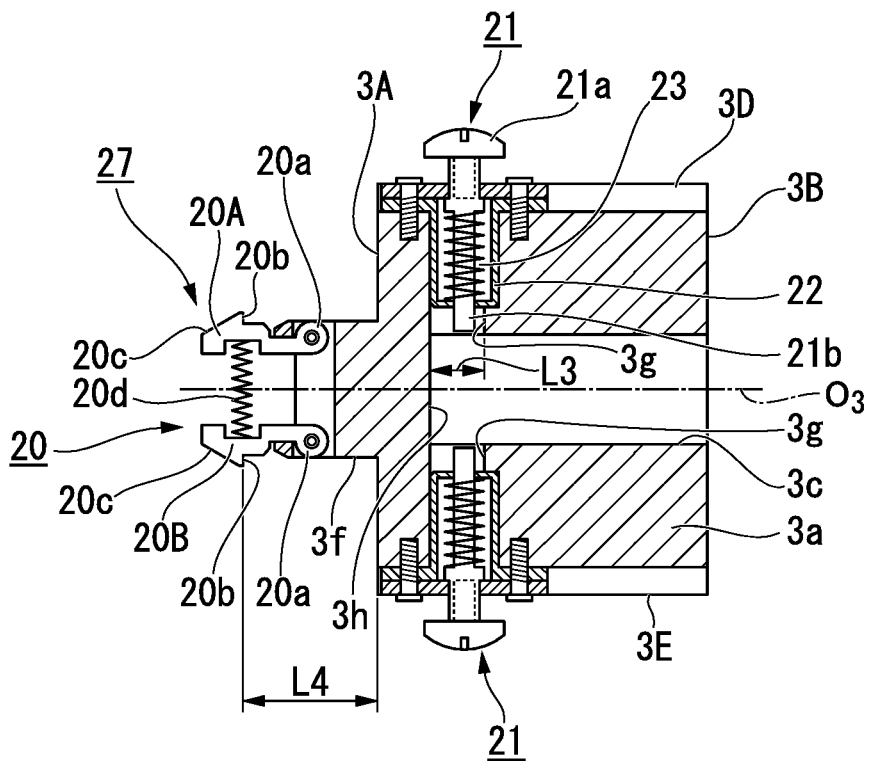
FIG. 8 is a cross-sectional view taken along line E-E of FIG. 7.
Figure 9:
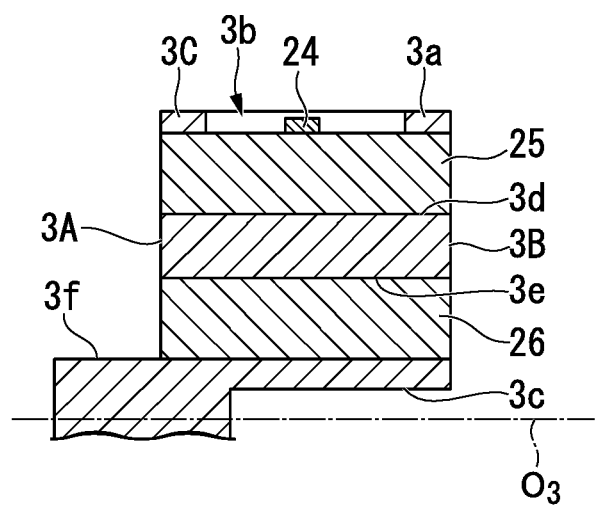
FIG. 9 is a cross-sectional view taken along line D-D of FIG. 7.
Figure 10:
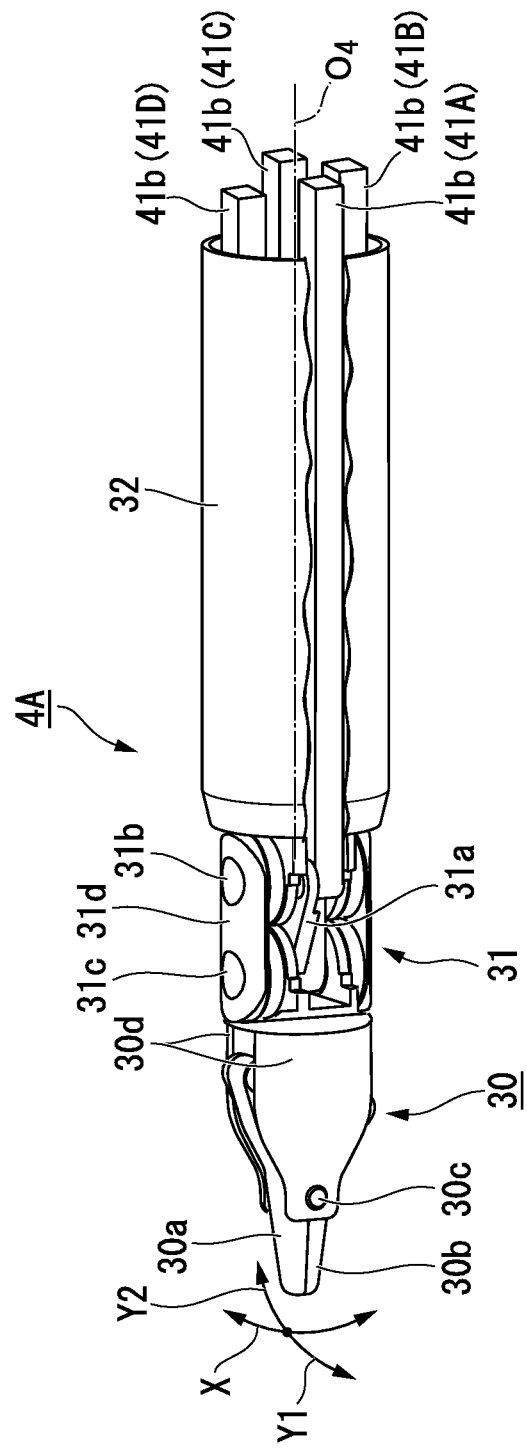
FIG. 10 is a schematic perspective view of the surgical instrument unit of the medical manipulator according to the first embodiment of the present invention.
Figure 11:
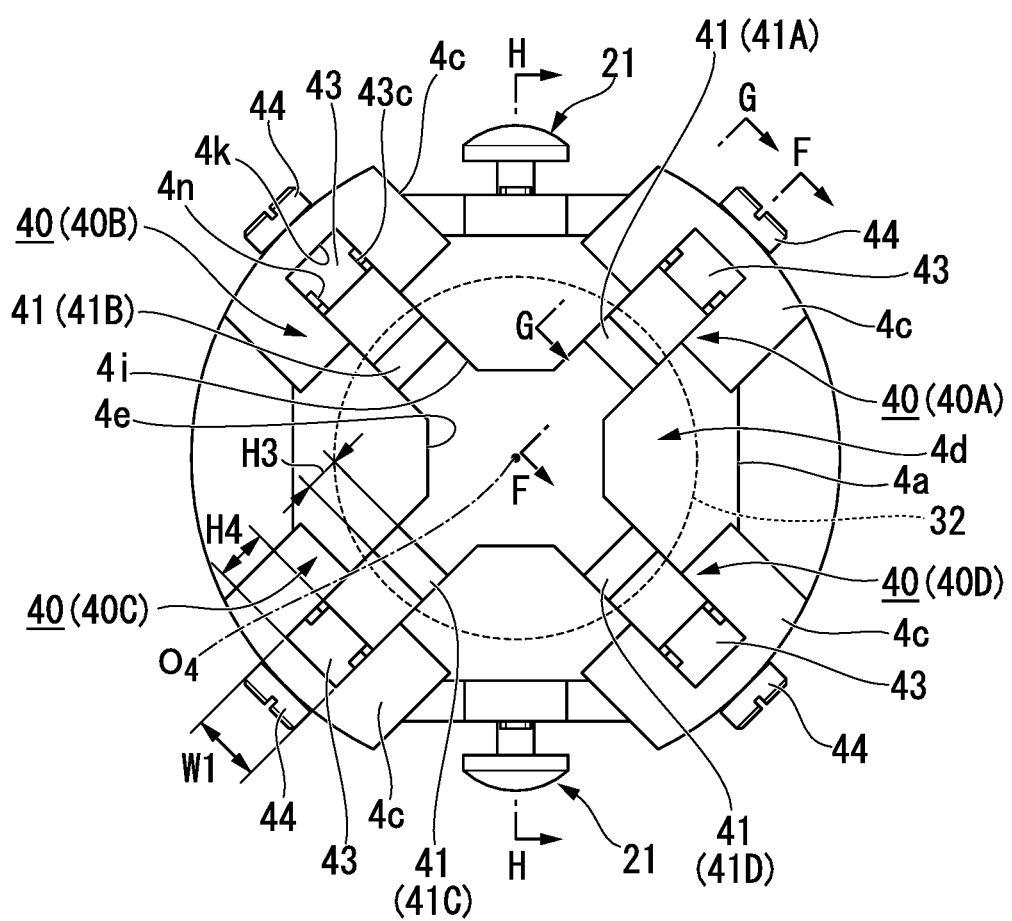
FIG. 11 is a schematic side view of a proximal end side of the surgical instrument unit of the medical manipulator according to the first embodiment of the present invention.
Figure 12:
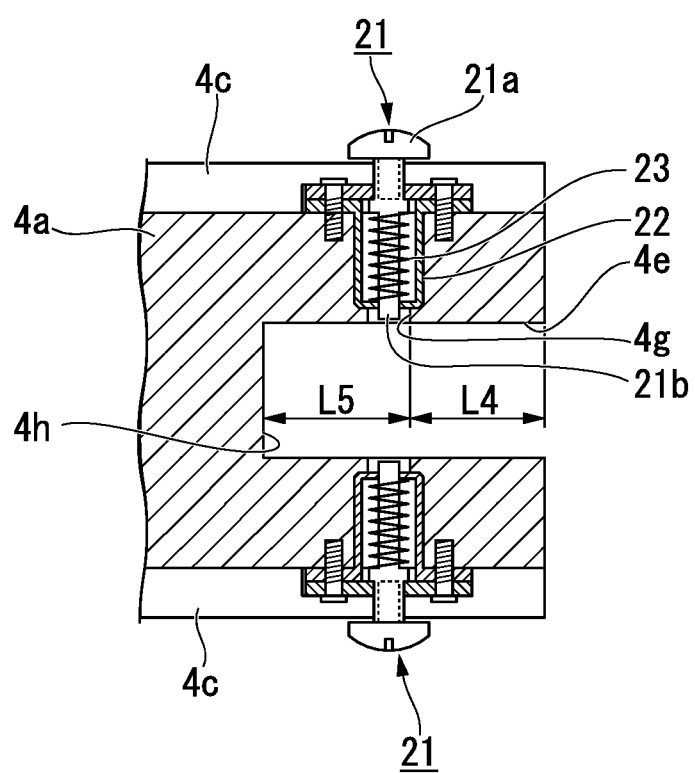
FIG. 12 is a cross-sectional view taken along line H-H of FIG. 11.
Figure 13A:
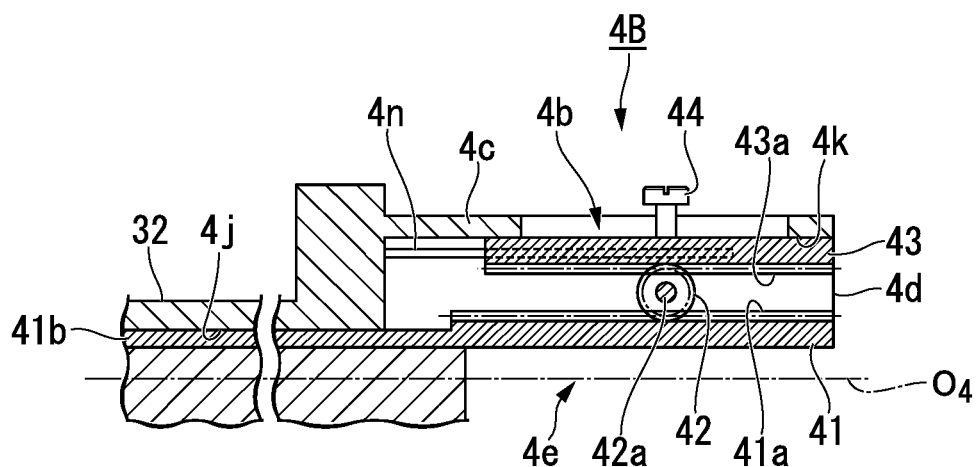
FIG. 13A is a cross-sectional view taken along line F-F of FIG. 11.
Figure 13B:
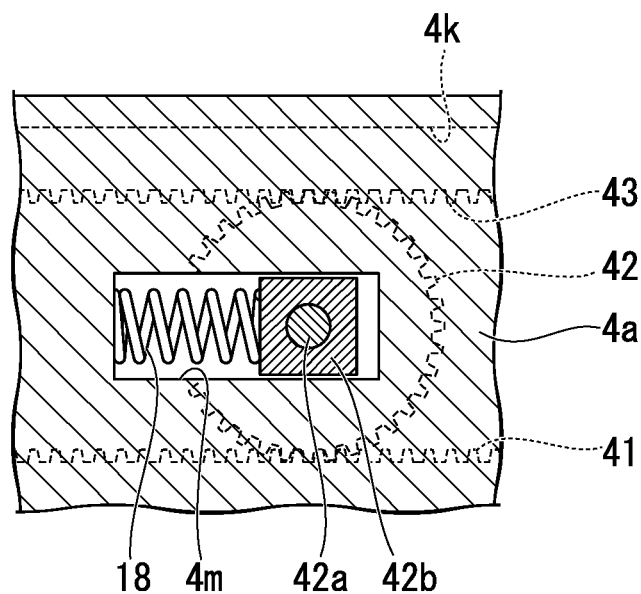
FIG. 13B is a cross-sectional view taken along line G-G of FIG. 11.
Figure 14:
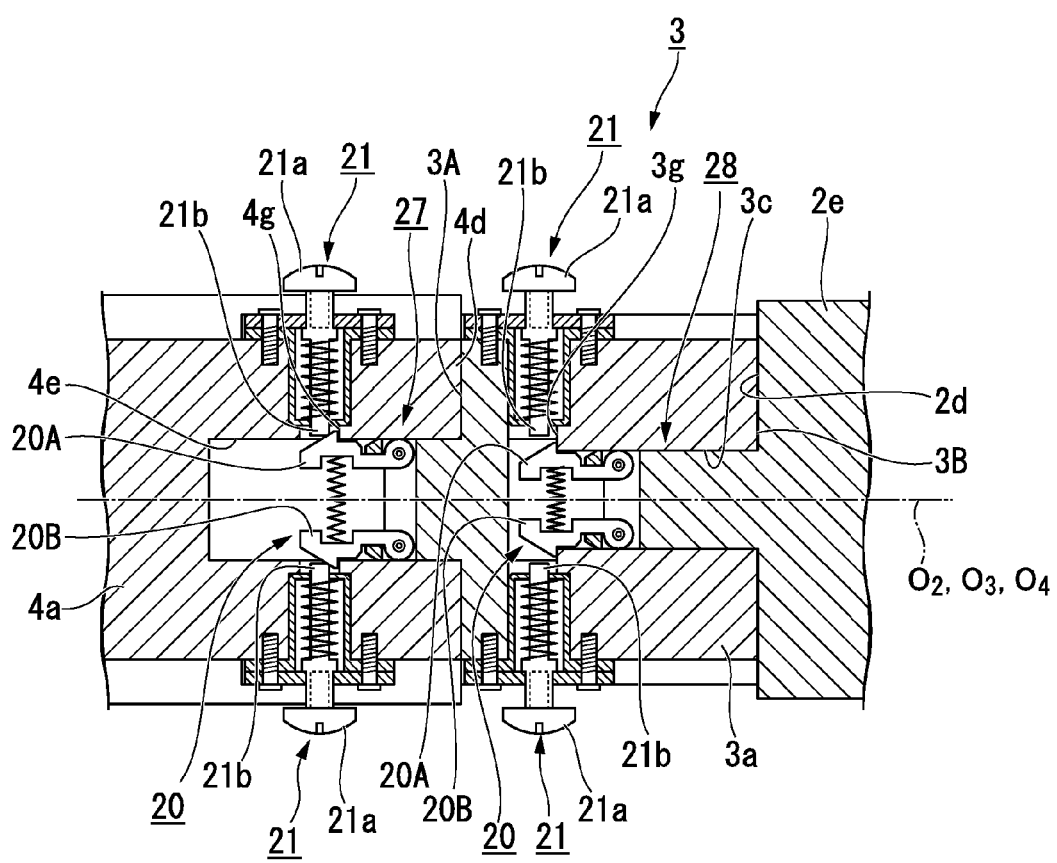
FIG. 14 is a cross-sectional view taken along line J-J of FIG. 2.
Figure 15:
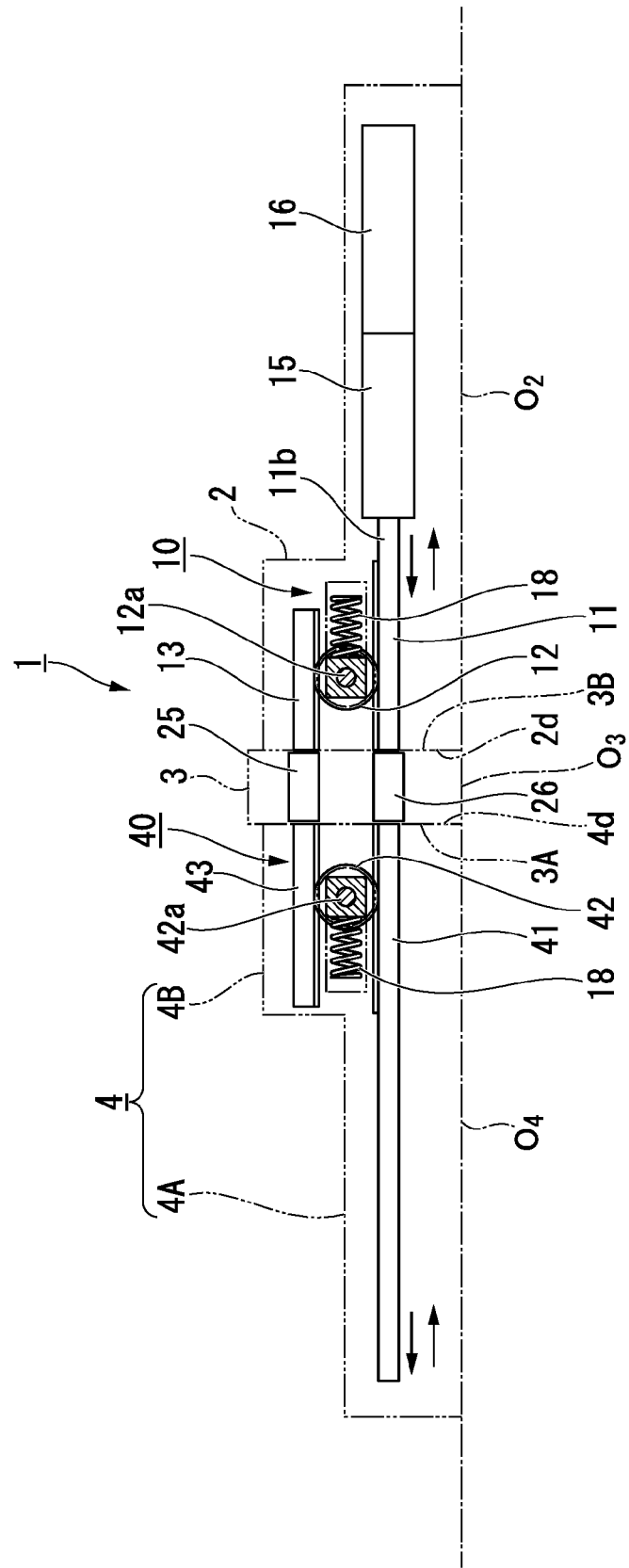
FIG. 15 is a schematic view of major parts of the medical manipulator according to the first embodiment of the present invention.

FIG. 2 is a schematic plan view showing a configuration of a medical manipulator according to a first embodiment of the present invention. FIG. 3 is a schematic side view of a distal end side of a surgical instrument drive unit of the medical manipulator according to the first embodiment of the present invention. FIG. 4 is a cross-sectional view taken along line B-B of FIG. 3. FIG. 5 is a cross-sectional view taken along line A-A of FIG. 3. FIG. 6 is a cross-sectional view taken along line C-C of FIG. 3. FIG. 7 is a schematic side view of a distal end side of an intermediate member of the medical manipulator according to the first embodiment of the present invention. FIG. 8 is a cross-sectional view taken along line E-E of FIG. 7. FIG. 9 is a cross-sectional view taken along line D-D of FIG. 7. FIG. 10 is a schematic perspective view of the surgical instrument unit of the medical manipulator according to the first embodiment of the present invention. FIG. 11 is a schematic side view of a proximal end side of the surgical instrument unit of the medical manipulator according to the first embodiment of the present invention. FIG. 12 is a cross-sectional view taken along line H-H of FIG. 11. FIG. 13A is a cross-sectional view taken along line F-F of FIG. 11. FIG. 13B is a cross-sectional view taken along line G-G of FIG. 11. FIG. 14 is a cross-sectional view taken along line J-J of FIG. 2. FIG. 15 is a schematic view of major parts of the medical manipulator according to the first embodiment of the present invention.

A medical manipulator 1 according to the embodiment shown in FIG. 2 can be used instead of the slave arm, to which the surgical instrument is attached, in the medical manipulator system.

The medical manipulator 1 may include the same joint and arm structure as the proximal end side of the slave arm at a proximal end portion thereof, and the entire slave arm may be replaced with a new one. However, hereinafter, as an example, a configuration in which a portion of the distal end side rather than the joint of the slave arm 200a is replaced with a new one, will be exemplarily described.

That is, as the medical manipulator 1 described below is detachably provided at a distal end portion of a joint arm support mechanism (not shown) having the same joint and arm structure as the proximal end side of the slave arm, the entire configuration of the slave arm can be replaced with a new one.

As described above, in the medical manipulator system, for example, the medical manipulator 1 can be installed instead of the surgical instrument 240a, the adaptor 220a, and the slave arm 200a.

For example, the medical manipulator 1 includes a surgical instrument drive unit 2, an intermediate member 3, and a surgical instrument unit 4, which correspond to a portion of the distal end side of the slave arm 200a, the adaptor 220a, and the surgical instrument 240a, respectively.

Hereinafter, when a relative positional relation in a longitudinal direction of the medical manipulator 1 is represented, unless specifically limited, as described above, a side directed to a body cavity of the patient P in use is referred to as a distal end side, and an opposite side is referred to as a proximal end side.

The surgical instrument drive unit 2 is provided at the proximal end side of the medical manipulator 1, and has substantially a shaft shape extending from the proximal end side to the distal end side as a whole.

In addition, the surgical instrument drive unit 2 includes a base section 2e disposed at the distal end side and detachably connected to the proximal end side of the intermediate member 3, and a housing 2a having a columnar shape formed at the proximal end side.

For example, materials of the base section 2e and the housing 2a may be a synthetic resin or metal.

A connecting end surface 2d abutting a connecting end surface 3B of the proximal end side of the intermediate member 3, which will be described later, is formed at the distal end side of the base section 2e.

As shown in FIG. 3, in the present embodiment, an appearance of the base section 2e is an octagonal prism shape having a size smaller than that of the housing 2a at a position which is on the same axis as a central axis $O_2$ of the housing 2a. As shown in FIG. 4, a connecting convex section 28 to be connected to the intermediate member 3 is provided at a center portion of the connecting end surface 2d to protrude toward the distal end side.

Hereinafter, for the purpose of brief description, a direction along a central axis of the surgical instrument drive unit 2 (in the embodiment, defined as the central axis $O_2$ of a housing) may be referred to as an axial direction, a direction intersecting the central axis in a plane perpendicular to the central axis may be referred to as a radial direction, and a circumferential direction of a circle about the central axis in the plane perpendicular to the central axis may be referred to as a circumferential direction. In addition, when relative far and near positions in the radial direction with respect to the central axis are represented, terms such as an outer circumferential side or an outside in the radial direction, an inner circumferential side or an inside in the radial direction, or the like, may be used.

Further, the same terms may be used even in the other shaft-shaped member having a clear central axis (also including a substantially shaft-shaped member).

The connecting convex section 28 includes an octagonal prism-shaped engagement protrusion section 2f extending from the connecting end surface 2d to the distal end side in the axial direction, and an engagement section 20 provided at the distal end side of the engagement protrusion section 2f.

The engagement section 20 includes engagement arm sections 20A and 20B turnably fixed by a turning support 20a and provided to be opposite to each other, and a coil spring 20d.

Both of the engagement arm sections 20A and 20B are inserted between a pair of stoppers 2h extending to the distal end side of the engagement protrusion section 2f in an extension direction of the engagement protrusion section 2f and provided at the distal end of the engagement protrusion section 2f.

The coil spring 20d is an elastic member disposed between distal end portions of the engagement arm sections 20A and 20B to bias the engagement arm sections 20A and 20B outward in opposite directions. For this reason, the engagement arm sections 20A and 20B are biased to the outside of the side surfaces of the engagement protrusion section 2f about the respective turning supports 20a by the coil spring 20d to be pressed to the inside of the stoppers 2h.

Flat sections aligned with the side surfaces of the engagement protrusion section 2f while pressed against the stoppers 2h are formed at the distal end portions of the engagement arm sections 20A and 20B. Engagement claw sections 20b, which are stepped sections protruding to the outward of the side surfaces of the engagement protrusion section 2f, are formed at the distal ends of the flat sections.

Positions in the axial direction of the engagement claw sections 20b have a distance L1 from the connecting end surface 2d in a state in which the engagement arm sections 20A and 20B are pressed to the stoppers 2h.

An inclination section 20c inclined in a direction directed to the central axis $O_2$ extends from an apex in a protrusion direction of the engagement claw section 20b to the distal end side within a range of a distance L2. A width between the distal ends of the inclination sections 20c is smaller than a width of the engagement protrusion section 2f.

In addition, as shown in FIG. 3, a second input member accommodating section 2c configured to accommodate a second input member 13 (described later) protruding outward in the radial direction is formed at an outer circumferential side of the base section 2e. In the embodiment, four second input member accommodating sections 2c are provided at alternate side surfaces of the base section 2e of an octagonal prism.

An appearance in the radial direction of each of the second input member accommodating sections 2c is aligned with an appearance of a cylindrical shape of the housing 2a.

A reciprocation drive unit 10 is provided at each of the second input member accommodating sections 2c in the inside of the base section 2e and each of the second input member accommodating sections 2c. Configurations of the reciprocation drive units 10 are the same as in the embodiment. When the reciprocation drive units 10 are distinguished from each other, reciprocation drive units 10A, 10B, 10C, and 10D may be referred to clockwise as shown in FIG. 3.

As shown in FIG. 5, the reciprocation drive unit 10 includes a first input member 11 (one of input members), a rotation-translation transduction unit 15 (a driving source), a motor 16 (a driving source), a second input member 13 (the other of the input members), and a pinion 12 (an inversion interlocking member of drive unit, a second inversion interlocking member).

The first input member 11 is a rod-shaped member configured to advance and retract in a direction of the central axis $O_2$ toward the intermediate member 3 connected to the connecting end surface 2d, and transmitting a driving force upon the advance. In the embodiment, the first input member 11 is entirely formed in an angled rod shape and has a cross-sectional shape of width W1×thickness H1. However, a rack section 11a is formed at one side surface of a distal end side of the first input member 11.

A material of the first input member 11 may be a material having stiffness appropriate to transmit a driving force, for example, a metal material.

A portion of the distal end side of the first input member 11 is accommodated in a guide groove 2k, configured to slidably hold the first input member 11, in a state in which the rack section 11a is directed outward in the radial direction.

The guide groove 2k is a groove section extending to penetrate in the axial direction parallel to the central axis $O_2$ in a portion of the base section 2e disposed at the outer circumferential side rather than the engagement protrusion section 2f.

In addition, a portion of the proximal end side of the first input member 11 extends inside the housing 2a and is supported to advance and retract by a plurality of slide bearings 17 disposed in the housing 2a.

The rotation-translation transduction unit 15 and the motor 16 constitute a driving source configured to advance and retract the first input member 11 and the second input member 13 in a direction along the central axis $O_2$, and are fixed into the housing 2a.

The rotation-translation transduction unit 15 is provided between an end of the most proximal end side of the first input member 11 and a rotary shaft 16a of the motor 16, and converts rotation movement of the motor 16 into translation acting movement in the direction along the central axis $O_2$.

A configuration of the rotation-translation transduction unit 15 is not particularly limited as long as rotation movement can be converted into translation acting movement. In the present embodiment, a lead screw mechanism is employed as one example.

The motor 16 is electrically connected to the slave control circuit 400, and varies a rotation direction and a rotation angle of the rotary shaft 16a in accordance with a control signal from the slave control circuit 400. For example, a DC motor or the like can be employed as the motor 16.

The second input member 13 is a rod-shaped member configured to advance and retract in a direction along the central axis $O_2$ toward the intermediate member 3 connected to the connecting end surface 2d and transmitting a driving force upon the advance. In the present embodiment, the second input member 13 is entirely formed in a substantially angled rod shape and has a cross-sectional shape of width W1×thickness H2. However, a rack section 13a having the same shape as the rack section 11a of the first input member 11 is formed at one side surface of the second input member 13.

A material of the second input member 13 may be a material having stiffness appropriate to transmit a driving force, for example, a metal material.

A stopper pin 14 configured to restrict an advance/retract amount of the second input member 13 is formed so as to protrude at a side surface of a rear surface of the rack section 13a.

The second input member 13 including the above-mentioned configuration is accommodated in a guide groove 2j configured to slidably hold the second input member 13 in a state in which the rack section 13a is directed inward in the radial direction.

The guide groove 2j is a groove section extending to penetrate in a direction along the central axis $O_2$ in the second input member accommodating section 2c. The guide groove 2j has a groove bottom surface configured to slide on a side surface of the second input member 13 opposite to the rack section 13a of the second input member 13, and a groove side surface configured to guide a side surface near the rack section 13a of the second input member 13.

The stopper groove 2b having an elongated hole shape in a groove longitudinal direction penetrates through a groove bottom surface of the guide groove 2j. The stopper pin 14 of the second input member 13 is inserted into the stopper groove 2b.

For this reason, an advance and retraction range of the second input member 13 is restricted by an opening amount in a longitudinal direction of a stopper groove 2b.

A convex section 2m protruding toward the second input member 13 is provided at a groove side surface of the guide groove 2j exclusive of a distal end side of the guide groove 2j. A range in which the convex section 2m is not provided is a range in which a second intermediate transmission member 25 (to be described later) may advance from the connecting end surface 2d.

Meanwhile, a stepped section 13c engaged with the convex section 2m is formed at a side surface of the second input member 13. For this reason, when the second input member 13 advances or retracts, the side surface of the second input member 13 opposite to the rack section 13a is in close contact with and slides with respect to the groove bottom surface of the guide groove 2j.

The guide grooves 2k and 2j may be configured as two separate guide holes having a rectangular shape matching appearances of the first input member 11 and the second input member 13, respectively. In the present embodiment, the guide grooves 2k and 2j are configured to be in communication with each other in the radial direction and have a long rectangular hole in the radial direction as a whole. That is, the guide groove 2k is formed at an inner end in the radial direction of the rectangular hole, and the guide groove 2j is formed at an outer end in the radial direction.

For this reason, when a rod-shaped member has a width equal to or less than a width W1 in the circumferential direction of the guide grooves 2k and 2j, a rod-shaped member having a larger cross-sectional area than the first input member 11 and the second input member 13 can be inserted into the guide grooves 2k and 2j.

The pinion 12 is a gear engaged with the rack section 11a of the first input member 11 and the rack section 13a of the second input member 13.

The rotary shaft 12a of the pinion 12 is turnably supported at a substantially constant position from the connecting end surface 2d and biased to the distal end side of the surgical instrument drive unit 2.

In the present embodiment, as shown in FIG. 6, in the second input member accommodating section 2c and the base section 2e configured to cover the pinion 12 from a side portion thereof, a guide hole 2g extending in a direction along the central axis $O_2$ (not shown in FIG. 6, see FIG. 5) is provided. A rotary shaft 12a is turnably supported by a sliding block 12b slidably held in the guide hole 2g.

The sliding block 12b is biased toward the distal end side by a coil spring 18 (a biasing unit of drive unit) disposed at the proximal end side (a right side of FIG. 6) in the guide hole 2g.

For this reason, since the pinion 12 is biased to the distal end side even when a backlash occurs between the rack sections 11a and 13a, the pinion 12 is engaged with the rack sections 11a and 13a with no backlash.

In addition, the coil spring 18 in the guide hole 2g biases the entire of the first input member 11 and the second input member 13 to the distal end sides.

In the present embodiment, as shown in FIG. 3, two sets of reciprocation drive units 10 including the above-mentioned configuration are provided to oppose each other in two axial directions perpendicular to the central axis $O_2$. In addition, in any reciprocation drive unit 10, the first input member 11 is disposed at a center side of the connecting end surface 2d in comparison with the second input member 13. Further, when a direction combining the first input member 11 and the second input member 13 in the connecting end surface 2d is defined as a disposition direction of the reciprocation drive unit 10, the respective reciprocation drive units 10 are radially disposed about the central axis $O_2$.

The intermediate member 3 detachably connects the surgical instrument drive unit 2 and the surgical instrument unit 4, and transmits a driving force from the surgical instrument drive unit 2 toward the surgical instrument unit 4.

As shown in FIG. 7, the intermediate member 3 includes an intermediate member main body 3a, a first intermediate transmission member 26, and the second intermediate transmission member 25.

The intermediate member main body 3a includes the connecting end surface 3B (a drive unit side end) in close contact with and abutting the connecting end surface 2d of the surgical instrument drive unit 2, and a connecting end surface 3A (a surgical instrument unit side end) in close contact with and abutting a connecting end surface 4d (described later) of the surgical instrument unit 4 disposed parallel to the connecting end surface 3B, at both ends thereof.

The intermediate member main body 3a has a shape in which a circle aligned with the housing 2a is cut by two parallel lines, when seen from a side view. The intermediate member main body 3a is a substantially shaft-shaped member extending along a central axis $O_3$, which is a straight line passing through a center line of a circle aligned with the housing 2a. For this reason, the intermediate member main body 3a includes the curved side surface 3C curved in an arc shape, and flat side surfaces 3D and 3E formed of planes.

An engagement hole section 3c configured such that the engagement protrusion 2f of the surgical instrument drive unit 2 is inserted and fixing a position in the radial direction of the surgical instrument drive unit 2 with respect to the intermediate member 3 extends along the central axis $O_3$ in a center section of the connecting end surface 3B as shown in FIG. 8.

A locking surface 3g extending to the outward of the engagement hole section 3c at a position of the distance L1 from the connecting end surface 3B is provided in the engagement hole section 3c. A hole depth surface 3h of the engagement hole section 3c is disposed at a distal end side of the locking surface 3g by a distance L3. The distance L3 is a dimension larger than the distance L2 of the distal end side rather than the engagement claw section 20b of the engagement section 20.

As the above-mentioned configuration is provided, when the connecting convex section 28 is inserted into the engagement hole section 3c from the proximal end side, a force of reducing a facing gap between the engagement arm sections 20A and 20B is applied from the engagement hole section 3c via the inclination sections 20c of the engagement arm sections 20A and 20B. Then, as the coil spring 20d is pushed into the engagement hole section 3c, the coil spring 20d is compressed to be inserted into the engagement hole section 3c.

When the engagement section 20 is pushed into the distal end side rather than the locking surface 3g, the respective engagement claw sections 20b biased by the coil spring 18 protrude outward in the radial direction to be locked to the locking surface 3g. Accordingly, the surgical instrument drive unit 2 is connected to the intermediate member 3 (see FIG. 14).

As shown in FIG. 8, a connecting convex section 27 configured to be connected to the surgical instrument unit 4 protruding toward the distal end side is provided at a center portion of the connecting end surface 3A.

The connecting convex section 27 has an octagonal prism shape extending from the connecting end surface 3A to the distal end side in the axial direction. The connecting convex section 27 includes an engagement protrusion section 3f having the same pair of stoppers 2h as of the engagement protrusion section 2f is provided at the distal end side, and the engagement section 20 having the same shape as described above and formed at the distal end side of the engagement protrusion section 3f.

An appearance or a size of the engagement protrusion section 3f may be the same as that of the engagement protrusion section 2f. In the present embodiment, it is different in that a distance L4 from the connecting end surface 3A to the engagement claw section 20b is smaller than the distance L1 from the connecting end surface 2d of the connecting convex section 28 to the engagement claw section 20b.

Opposite directions of the engagement arm sections 20A and 20B of the engagement section 20 in the engagement protrusion section 3f pass the central axis $O_3$ and are perpendicular to the flat side surfaces 3D and 3E.

Release buttons 21 configured to advance and retract in the radial direction between the locking surface 3g and the hole depth surface 3h are provided at the flat side surfaces 3D and 3E, respectively.

The release button 21 is a member in which a manipulation unit 21a is provided at one end of a shaft section 21b and configured to release connection to the surgical instrument drive unit 2. The other end of the shaft section 21b is inserted into a center of the intermediate member main body 3a. The manipulation unit 21a is disposed to protrude outward from the flat side surface 3D (3E).

The shaft section 21b is inserted into a holder member 22 inserted into the intermediate member main body 3a, and biased outward in the radial direction of the intermediate member main body 3a by a coil spring 23 disposed in the holder member 22.

A length of the shaft section 21b is set such that the other end of the shaft section 21b is retracted outward in the radial direction more than the inner circumferential surface of the engagement hole section 3c when an external force is not applied to the manipulation unit 21a, and the other end of the shaft section 21b protrudes from the inner circumferential surface of the engagement hole section 3c when the manipulation unit 21a is pressed to be pushed into the intermediate member main body 3a.

As shown in FIG. 7, four guide holes 3e (first guide sections) and a guide hole 3d (a second guide section) penetrating in a direction along the central axis $O_3$ are provided between the connecting end surfaces 3A and 3B. These guide holes 3e and 3d are radially disposed about the central axis $O_3$. In the present embodiment, the guide holes 3e and 3d are provided along two axes passing through the central axis $O_3$ and perpendicular to each other by one set.

The guide hole 3e is a through-hole formed at a position opposite to a distal end surface and the guide groove 2k of the first input member 11 of the surgical instrument drive unit 2 when the surgical instrument drive unit 2 is connected thereto. In the present embodiment, the guide hole 3e is an angled hole having a rectangular cross-sectional shape of width W1×thickness h1. Here, the width is a dimension in the circumferential direction, and the thickness is a dimension in the radial direction. The thickness h1 is set to be a dimension equal to or larger than a thickness H1 of the first input member 11.

The first intermediate transmission member 26 having an angled rod shape with the same rectangular cross-sectional shape as the guide hole 3e is slidably inserted into the guide hole 3e.

The guide hole 3d is a through-hole formed at a position opposite to a distal end surface of the second input member 13 of the surgical instrument drive unit 2 when the surgical instrument drive unit 2 is connected thereto. In the present embodiment, the guide hole 3d is an angled hole having a rectangular cross-section of width W1×thickness h2. Here, the width is a dimension in the circumferential direction, and the thickness is a dimension in the radial direction. The thickness h2 is set to a dimension equal to or larger than a thickness H2 of the second input member 13.

The second intermediate transmission member 25 having an angled rod shape with the same rectangular cross-sectional shape as the guide hole 3d is slidably inserted into the guide hole 3d.

As shown in FIG. 9, in a center portion in the longitudinal direction of each of the guide holes 3d, a stopper groove 3b having a long hole shape and penetrating the guide hole 3d is formed between each of the guide holes 3d and a curved side surface 3C. A retaining pin 24 protruding from one side surface of the second intermediate transmission member 25 is inserted into the stopper groove 3b.

For this reason, a range in which the second intermediate transmission member 25 is able to advance and retract is restricted by an opening amount in the longitudinal direction of the stopper groove 3b.

In addition, as shown in FIG. 9, a length of the first intermediate transmission member 26 and a length of the second intermediate transmission member 25 are equal to a distance between the connecting end surface 3A and the connecting end surface 3B.

A material of both of the first intermediate transmission member 26 and the second intermediate transmission member 25 may be a metal or synthetic resin having stiffness appropriate to transmit a driving force.

The surgical instrument unit 4 is a member having an effector configured to manipulate a target object, driving the effector by a driving force transmitted from the surgical instrument drive unit 2 via the intermediate member 3, and manipulating the target object. The surgical instrument unit 4 is detachably provided on the connecting end surface 3A of the intermediate member 3.

The effector of the surgical instrument unit 4 can employ an appropriate effector when the effector can be operated by the driving force in one axial direction transmitted by the first intermediate transmission member 26 and the second intermediate transmission member 25, which advance and retract with respect to the surgical instrument unit 4.

Hereinafter, an example in which the surgical instrument unit 4 is a grasping forceps, and a forceps section and a joint are provided as an effector will be exemplarily described.

As shown in FIG. 2, the surgical instrument unit 4 has substantially a shaft shape as a whole, and includes a surgical instrument main body 4A and a driving force transmission section 4B along a central axis $O_4$ from the distal end side.

As shown in FIG. 10, the surgical instrument main body 4A includes a forceps section 30 (an effector), a joint 31 (an effector), and a shaft section 32 from the distal end side.

The forceps section 30 includes forceps pieces 30a and 30b which turn about a pivotal shaft 30c fixed to a cover member 30d. An end of a wire (not shown) is connected to the proximal end side of the forceps pieces 30a and 30b, and the other end of the wire is inserted into distal end shaft sections 41b, which are distal end portions of first transmission members 41D and 41B, the shaft section 32 and the joint 31, and connected thereto.

The forceps pieces 30a and 30b are connected to the first transmission members 41D and 41B by wires (not shown). For this reason, when the first transmission member 41D is retracted to the proximal end side, the forceps piece 30a is opened, and when the first transmission member 41B is retracted to the proximal end side, the forceps piece 30b is opened. On the other hand, when the first transmission member 41D is advanced to the distal end side, the forceps piece 30a is closed, and when the first transmission member 41B is advanced to the distal end side, the forceps piece 30b is closed. As the forceps piece 30a and the forceps piece 30b are closed to contact each other, the forceps is closed.

In addition, when the first transmission member 41D is retracted to the proximal end side and the first transmission member 41B is advanced to the distal end side, the forceps pieces 30a and 30b turn in a direction of an arrow Y2. On the other hand, when the first transmission member 41D is advanced to the distal end side and the first transmission member 41B is retracted to the proximal end side, the forceps pieces 30a and 30b turn in a direction of an arrow Y1.

The joint 31 turns the forceps section 30 in a direction perpendicular to the axial direction of the shaft section 32. In the joint 31, a driven shaft 31c provided at the proximal end portion of the forceps section 30 is connected to a turning spindle 31b provided at the distal end portion of the shaft section 32 by a turning arm 31d.

An end of a distal end side of a drive link 31a is connected to the driven shaft 31c. In addition, a distal end portion of a first transmission member 41A inserted into the shaft section 32 is turnably connected to the end of the proximal end side of the drive link 31a. Further, the drive link 31a is also turnably connected to the turning spindle 31b.

For this reason, as the first transmission member 41A is advanced and retracted, the drive link 31a turns the driven shaft 31c about the turning spindle 31b, and the forceps section 30 is interlocked with the driven shaft 31c to be turned in a direction of an arrow X.

The first transmission member 41C is connected to the cover member 30d to maintain an orientation of the forceps section 30 by a link (not shown).

The shaft section 32 has a column-shaped appearance about the central axis $O_4$. The respective distal end shaft sections 41b of the first transmission members 41A, 41B, 41C, and 41D (described later) are inserted into the shaft section 32. The proximal end side of the shaft section 32 is connected to the driving force transmission section 4B.

The respective distal end shaft sections 41b are disposed at positions at which a circumference about the central axis $O_4$ of the shaft section 32 is divided into four parts. The distal end shaft sections 41b are held to advance and retract in the shaft section 32 by a guide hole 4j (see FIG. 13A) or the like.

As shown in FIG. 2, the driving force transmission section 4B includes a base section 4a disposed at the proximal end side and detachably connected to the distal end side of the intermediate member 3.

The connecting end surface 4d abutting the connecting end surface 3A of the intermediate member 3 is formed at the proximal end side of the base section 4a.

In the present embodiment, as shown in FIG. 11, an appearance of the base section 4a is an octagonal prism shape having an appearance larger than that of the shaft section 32 at a position which is disposed on the same axis as the central axis $O_4$. As shown in FIG. 12, an engagement hole section 4e configured to be connected to the connecting convex section 27 of the intermediate member 3 extends from a center portion of the connecting end surface 4d to the distal end side.

In addition, a second transmission member accommodating section 4c configured to accommodate a second transmission member 43 (described later) protrudes outward in the radial direction from the outer circumferential side of the base section 4a. In the present embodiment, four second transmission member accommodating sections 4c are alternately provided on the side surfaces of the base section 4a formed in an octagonal prism shape.

An appearance in the radial direction of each of the second transmission member accommodating sections 4c is aligned with an appearance of a cylindrical shape of the curved side surface 3C of the intermediate member 3 upon connection.

A locking surface 4g extending from a position of the distance L4 from the connecting end surface 4d to the outward of the engagement hole section 4e at a position is formed in the engagement hole section 4e. A hole depth surface 4h of the engagement hole section 4e is disposed at a position distal end side from the locking surface 4g by a distance L5. The distance L5 is formed to a dimension larger than the distance L2 of the distal end side of the engagement section 20 rather than the engagement claw section 20b.

According to the above-mentioned configuration, when the connecting convex section 27 of the intermediate member 3 is inserted into the engagement hole section 4e from the proximal end side, a force for reducing a facing gap between the engagement arm sections 20A and 20B is applied from the engagement hole section 4e via the inclination sections 20c of the engagement arm sections 20A and 20B. Then, the connecting convex section 27 is pushed into the engagement hole section 4e to compress the coil spring 20d, and the connecting convex section 27 is inserted into the engagement hole section 4e.

When the engagement section 20 is pushed into the distal end side rather than the locking surface 4g, the respective engagement claw sections 20b biased by the coil spring 20d protrude outward in the radial direction to be locked to the locking surface 4g. Accordingly, the intermediate member 3 can be connected to the driving force transmission section 4B of the surgical instrument unit 4 (see FIG. 14).

The release buttons 21 configured to advance and retract in the radial direction between the locking surface 4g and the hole depth surface 4h are respectively provided at a pair of side surfaces opposite to each other with the central axis $O_4$ of the base section 4a interposed therebetween.

In the present embodiment, the release button 21 has the same configuration as that installed on the intermediate member 3.

For this reason, the shaft section 21b is set to a length such that, when an external force is not applied to the manipulation unit 21a, the other end of the shaft section 21b is retracted outward in the radial direction from the inner circumferential face of the engagement hole section 4e, and when the manipulation unit 21a is pressed to be pushed inward the base section 4a, the other end protrudes from the inner circumferential side of the engagement hole section 4e.

As shown in FIG. 11, a reciprocation drive unit 40 is provided in the base section 4a and the second transmission member accommodating sections 4c at each of the second transmission member accommodating sections 4c. While the configuration of each of the reciprocation drive units 40 is the same as in the present embodiment, when these are distinguished, these may be referred to as the reciprocation drive units 40A, 40B, 40C, and 40D counterclockwise in FIG. 11.

As shown in FIG. 13A, the reciprocation drive unit 40 includes a first transmission member 41, the second transmission member 43, and a pinion 42.

The first transmission member 41 is a rod-shaped member configured to receive a driving force from the first intermediate transmission member 26 upon advance of the first intermediate transmission member 26 of the intermediate member 3 connected to the connecting end surface 4d, move in a direction along the central axis $O_4$, and transmit the driving force to the forceps section 30 or the joint 31 connected to the distal end side.

For this reason, each of the first transmission members 41 is disposed at a position opposite to each of the first intermediate transmission members 26 upon connection of the intermediate member 3 and configured to advance and retract between the connecting end surface 4d and the connecting end surface 3A while abutting the first intermediate transmission member 26 opposite thereto.

In the present embodiment, the first transmission member 41 is configured in an angled rod shape as a whole, and has a cross-sectional shape of width W1×thickness H3. However, a rack section 41a is formed at one side surface of the proximal end side of the first transmission member 41. In addition, the thickness H3 is set to be equal to or smaller than the thickness h1 of the first intermediate transmission member 26. A material of the first transmission member 41 may employ a material having stiffness appropriate to transmit a driving force, for example, a metal material.

The distal end shaft section 41b having an angled rod shape with a rectangular cross-sectional and without the rack section 41a is formed at the distal end side of the first transmission member 41. The distal end shaft section 41b is inserted into a guide hole 4j of the shaft section 32 to advance or retract.

In addition, a portion of the proximal end side of the first transmission member 41, on which the rack section 41a is formed, is accommodated in a guide groove 4i having a width W1 and configured to slidably hold the first transmission member 41 in a state in which the rack section 41a is directed outward in the radial direction.

When members corresponding to the reciprocation drive units 40A, 40B, 40C, and 40D are referred to as the first transmission members 41A, 41B, 41C, and 41D, respectively, in the present embodiment, the first transmission members 41B and 41D transmit a driving force to the forceps section 30, and the first transmission members 41A and 41C transmit a driving force to the joint 31.

The second transmission member 43 is a rod-shaped member configured to receive a driving force from the second intermediate transmission member 25 upon advance of the second intermediate transmission member 25 of the intermediate member 3 connected to the connecting end surface 4*d*, and move in the same direction as the second intermediate transmission member 25 along the central axis $O_4$. In the present embodiment, the second transmission member 43 is configured in a substantially angled rod shape as a whole, and has a cross-sectional shape of width W1×thickness H4. However, a rack section 43*a* having the same shape as the rack section 41*a* of the first transmission member 41 is formed at one side surface of the second transmission member 43. In addition, the thickness H4 is set to be equal to or smaller than the thickness h2 of the second intermediate transmission member 25.

A material of the second transmission member 43 may be a material having stiffness appropriate to transmit a driving force, for example, a metal material.

A manipulation member 44 configured to restrict an advance and retract amount of the second transmission member 43 and manually manipulate a position of the second transmission member 43 from the outside protrudes from a side surface of the rear surface of the rack section 43*a* in the second transmission member 43.

The second transmission member 43 having the configuration mentioned above is accommodated in a guide groove 4*k* configured to slidably hold the second transmission member 43 in a state in which the rack section 43*a* is directed inward in the radial direction.

The guide groove 4*k* is a groove section penetrating in a direction along the central axis $O_4$ in the second transmission member accommodating section 4*c*. The guide groove 4*k* has a groove bottom surface in sliding contact with a side surface of the second transmission member 43 opposite to the rack section 43*a*, and a groove side surface configured to guide a side surface of the second transmission member 43 near the rack section 43*a*.

A stopper groove 4*b* having a long hole shape in a groove longitudinal direction penetrates the groove bottom surface of the guide groove 4*k*. The manipulation member 44 of the second transmission member 43 is inserted into the stopper groove 4*b*.

For this reason, a range in which the second transmission member 43 can advance and retract is restricted by an opening amount in the longitudinal direction of the stopper groove 4*b*.

A convex section 4*n* protruding toward the second transmission member 43 is formed at the groove side surface of the guide groove 4*k* except for the proximal end side of the guide groove 4*k*. A range in which the convex section 4*n* is not formed is a range in which the second intermediate transmission member 25 may advance from the connecting end surface 4*d*.

Meanwhile, a stepped section 43*c* engaged with the convex section 4*n* is formed at the side surface of the second transmission member 43. Accordingly, when the second transmission member 43 advances and retracts, the side surface of the second transmission member 43 opposite to the rack section 43*a* can be brought in close contact with and slide with respect to the groove bottom surface of the guide groove 4*k*.

The guide grooves 4*i* and 4*k* may be configured by two separate guide holes having a rectangular shape matching the appearances of the first transmission member 41 and the second transmission member 43. In the present embodiment, the guide grooves 4*i* and 4*k* are configured by rectangular cross-sectional grooves in communication with each other in the radial direction and opened toward the engagement hole section 4*e* to be elongated in the radial direction. That is, the guide groove 4*k* is formed at a groove bottom section inside the radial direction of the rectangular groove, and the guide groove 4*i* is formed at an opening section outside the radial direction.

For this reason, when the rod-shaped member has a width equal to or smaller than the width W1 in the circumferential direction, even though the rod-shaped member has a larger cross-sectional area than the first transmission member 41 and the second transmission member 43, the rod-shaped member can be inserted into the guide grooves 4*i* and 4*k*.

The pinion 42 is a gear engaged with the rack section 41*a* of the first transmission member 41 and the rack section 43*a* of the second transmission member 43.

A rotary shaft 42*a* of the pinion 42 is turnably supported at a substantially constant position from the connecting end surface 4*d* in state of being biased to the proximal end side of the surgical instrument unit 4.

In the present embodiment, as shown in FIG. 13B, a guide hole 4*m* extending in a direction along the central axis $O_4$ (not shown in FIG. 13B, see FIG. 13A) is formed in the second transmission member accommodating section 4*c* and the base section 4*a* configured to cover the pinion 42 from a side thereof. Then, the rotary shaft 42*a* is turnably supported by a sliding block 42*b* slidably held in the guide hole 4*m*.

The sliding block 42*b* is biased toward the proximal end side by the coil spring 18 (a biasing unit of surgical instrument unit) disposed at the distal end side (shown in a left side of FIG. 13B) in the guide hole 4*m*.

For this reason, even when a backlash occurs between the rack sections 41*a* and 43*a*, since the pinion 42 is biased to the proximal end side, the pinion is engaged with the rack sections 41*a* and 43*a* with no backlash.

In addition, the coil spring 18 in the guide hole 4*m* biases the entire of the first transmission member 41 and the second transmission member 43 to the proximal end sides.

In the present embodiment, two sets of reciprocation drive units 40 having the above-mentioned configuration are provided opposite each other in two axial directions perpendicular to the central axis $O_4$, as shown in FIG. 13A. In addition, in all of the reciprocation drive units 40, the first transmission member 41 is disposed at a center side of the connecting end surface 4*d* in comparison with the second transmission member 43. Further, when a direction of combining the first transmission member 41 and the second transmission member 43 in the connecting end surface 4*d* is defined as a disposition direction of the reciprocation drive unit 40, the respective reciprocation drive units 40 are disposed to form a radial shape about the central axis $O_4$ of the surgical instrument unit 4.

In addition, as shown in FIG. 14, when the connecting convex section 28 of the surgical instrument drive unit 2 is inserted into the engagement hole section 3*c* of the intermediate member 3 and the connecting convex section 27 of the intermediate member 3 is inserted into the engagement hole section 4*e* of the surgical instrument unit 4 so that the connecting end surfaces 2*d* and 3B are compressed to abut the connecting end surfaces 3A and 4*d*, respectively, the respective engagement sections 20 are locked to the locking surfaces 3*g* and 4*g*. As described above, in the present embodiment, the surgical instrument drive unit 2, the intermediate member 3, and the surgical instrument unit 4 are disposed on the same axes as the central axes $O_2$, $O_3$, and $O_4$, and the surgical instrument drive unit 2, the intermediate member 3, and the surgical instrument unit 4 are inserted in directions along the respective central axes, respectively, completing connection.

Accordingly, as shown in FIG. 1, the surgical instrument unit 4, the intermediate member 3 and the surgical instrument drive unit 2 are connected to assemble the medical manipulator 1.

Here, in the surgical instrument unit 4, the intermediate member 3, and the surgical instrument drive unit 2, positioning of the reciprocation drive unit 40, the guide holes 3d and 3e, and the reciprocation drive unit 10 positioned about the central axes $O_4$, $O_3$, and $O_2$ and radially disposed by the connecting convex sections 27 and 28 are aligned with each other.

For this reason, positions of groove bottom surfaces outside in the radial direction of the guide groove 4k, the guide hole 3d, and the guide groove 2j are aligned with positions of the respective groove side surfaces in the circumferential direction. In addition, positions of the groove bottom surfaces inside the radial direction of the guide groove 4i, the guide hole 3e, and the guide groove 2k are aligned with each other. Further, positions of the respective groove side surface in the circumferential direction of the guide groove 4i, the guide hole 3e, and the guide groove 2k are aligned with each other.

Furthermore, the respective reciprocation drive units 10 and 40 are opposite to each other via the second intermediate transmission member 25 and the first intermediate transmission member 26 of the intermediate member 3. In addition, the pinion 12 is biased to the distal end side by the coil spring 18 configured to bias the rotary shaft 12a, and the pinion 42 is biased to the proximal end side by the coil spring 18 configured to bias the rotary shaft 42a.

For this reason, as shown in FIG. 15, the distal end portion of the first input member 11 and the proximal end portion of the first transmission member 41 are brought in contact with the proximal end portion and the distal end portion of the first intermediate transmission member 26, respectively.

In addition, the distal end portion of the second input member 13 and the proximal end portion of the second transmission member 43 are brought in contact with the proximal end portion and the distal end portion of the second intermediate transmission member 25, respectively.

In action in use of the medical manipulator 1 having the above-mentioned configuration, the case in which the medical manipulator 1 is attached to one of the slave arms 200a to 200d, for example, the slave arm 200a, will be exemplarily described.

Figure 16A:
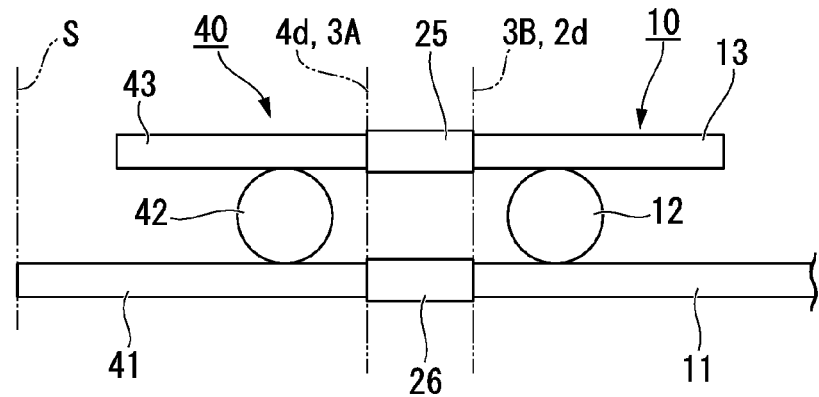
FIG. 16A is a view for schematically describing an action of major parts of the medical manipulator according to the first embodiment of the present invention.
Figure 16B:
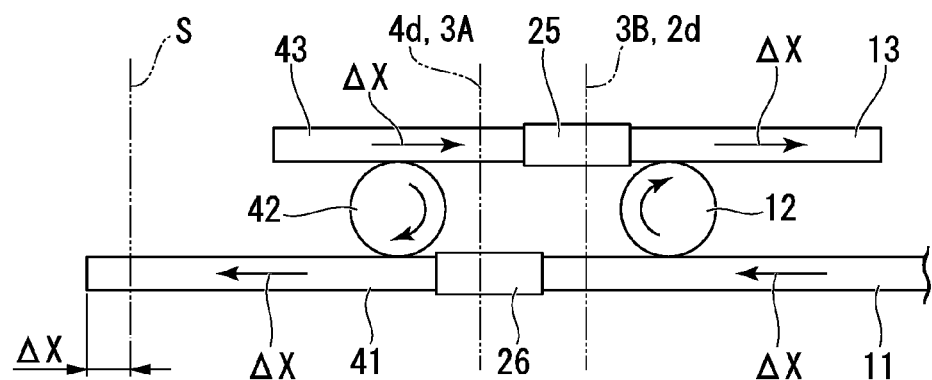
FIG. 16B is a view for schematically describing an action of major parts of the medical manipulator according to the first embodiment of the present invention.
Figure 16C:
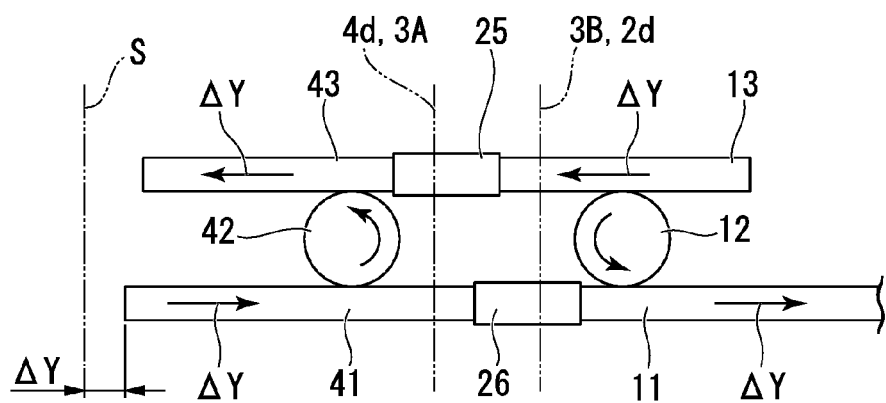
FIG. 16C is a view for schematically describing an action of major parts of the medical manipulator according to the first embodiment of the present invention.

FIGS. 16A, 16B, and 16C are views for describing schematic actions of major parts of the medical manipulator according to the first embodiment of the present invention.

First, in the medical manipulator system, the operator Op mounts the medical manipulator 1 assembled as described above on the medical manipulator system instead of the surgical instrument 240a, the adaptor 220a, and the slave arm 200a, and electrically connects the surgical instrument drive unit 2 to the slave control circuit 400. In addition, the operator Op connects surgical instruments 240b to 240d, which are other surgical instruments, to adaptors 220b to 220d as necessary.

When the operator Op performs predetermined manipulation on the corresponding master arm, the power unit of the slave arm is driven via the slave control circuit 400a. Power generated from the power unit is converted into translation acting movement or turning movement via the adaptor.

For example, when manipulation using the medical manipulator 1 is input, in accordance with the manipulation amount, the respective motors 16 of the surgical instrument drive unit 2 are rotated.

Rotation movement of each of the motors 16 is converted into corresponding translation acting movement by each of the rotation-translation transduction unit 15, and a proximal end shaft section 11b (see FIG. 15) of the first input member 11 connected to each of the rotation-translation transduction unit 15 advances and retracts in a direction along the central axis $O_2$.

When the motor 16 is stopped, as shown in FIG. 16A, in the connecting end surfaces 2d and 3B, the first input member 11 and the first intermediate transmission member 26 are opposite to the second input member 13 and the second intermediate transmission member 25, and in the connecting end surfaces 3A and 4d, the first intermediate transmission member 26 and the first transmission member 41 are opposite to the second intermediate transmission member 25 and the second transmission member 43.

The distal end portion of the first transmission member 41 connected to a link of an effector or the like is positioned at an initial position S.

In addition, in FIG. 16A, while not shown, all of the guide groove 4k, the guide hole 3d, and the guide groove 2j are aligned with the guide groove 4i, the guide hole 3e, and the guide groove 2k as described above. For this reason, the first input member 11 and the first intermediate transmission member 26, and the second input member 13 and the second intermediate transmission member 25 are configured to advance and retract to each other in the axial direction in the connecting end surfaces 2d and 3B. In addition, the intermediate transmission member 26 and the first transmission member 41, and the second intermediate transmission member 25 and the second transmission member 43 are configured to advance and retract to each other in the axial direction in the connecting end surfaces 3A and 4d.

First, as shown in FIG. 16B, the first input member 11 advances to the distal end side by ΔX. Here, the proximal end portion of the first intermediate transmission member 26 moves to the distal end side to receive the driving force by being pressed from the first input member 11.

In addition, the proximal end portion of the first transmission member 41 abutting the distal end side of the first intermediate transmission member 26 receives the driving force by being pressed from the first intermediate transmission member 26. Here, since compression stiffness of the first input member 11, the first intermediate transmission member 26, and the first transmission member 41 with respect to the driving force is sufficient great, even when a compression stress is generated in each of the members by a load of the effector, a compression deformation amount is negligible in comparison with ΔX. For this reason, the distal end of the first transmission member 41 also moves from the initial position S to the distal end side by ΔX.

Accordingly, the driving force is transmitted from the first transmission member 41 to the effector, and the effector is driven.

Meanwhile, when the first input member 11 and the first transmission member 41 move to the distal end side, the pinions 12 and 42 respectively engaged with the rack sections 11a and 41a are turned clockwise in the drawing. As a result, the driving forces transmitted to the first input member 11 and the first transmission member 41 are transmitted to the second input member 13 and the second transmission member 43 via the pinions 12 and 42.

Accordingly, the second input member 13 and the second transmission member 43 retract to the proximal end side in a direction opposite to the first input member 11 and the first transmission member 41 by ΔX, and the second intermediate transmission member 25 sandwiched therebetween also retracts to the proximal end side by ΔX.

Next, as shown in FIG. 16C, the first input member 11 is retracted from a state shown in FIG. 16A to the proximal end side by ΔY. Here, since the first input member 11 is separated from the proximal end portion of the first intermediate transmission member 26, the driving force is not directly transmitted from the first input member 11 to the first intermediate transmission member 26.

However, when the first input member 11 retracts, since the pinion 12 is turned counterclockwise in the drawing, the driving force is transmitted to the second input member 13, and the second input member 13 is moved to the distal end side by ΔY.

For this reason, as the distal end portion of the second input member 13 presses the proximal end portion of the second intermediate transmission member 25, the second intermediate transmission member 25 receives the driving force and advances to the distal end side by ΔY. Similarly, since the distal end portion of the second intermediate transmission member 25 presses the proximal end portion of the second transmission member 43, the driving force is transmitted to the second transmission member 43, and the second transmission member 43 advances to the distal end side by ΔY.

Here, the second transmission member 43 transmits the driving force even to the engaged pinion 42 to turn the pinion 42 counterclockwise also. For this reason, the driving force and the moving amount are inverted and transmitted to the first transmission member 41, and the first transmission member 41 retreats by ΔY.

Accordingly, the distal end portion of the first transmission member 41 retracts from the initial position S by ΔY, the driving force is transmitted to the effector, and the effector is driven.

Meanwhile, the distal end portion of the first intermediate transmission member 26 is pressed by the proximal end portion of the first transmission member 41, and retracted to the proximal end side by ΔY. For this reason, the first intermediate transmission member 26 retracts by ΔY, and an abutting state of the first intermediate transmission member 26 and the first input member 11 is maintained.

As described above, according to the medical manipulator 1 according to the present embodiment, even when the first input member 11 is advanced to the distal end side or retreated to the proximal end side, since the reciprocation drive units 10 and 40 have an action of inverting the driving force and the moving amount, the first transmission member 41 can follow movement of the first input member 11 to advance and retract.

In the medical manipulator 1, the first input member 11 and the second input member 13 are disposed to form a pair at the connecting end surface 2d, which is one end in an attachment and detachment direction of the surgical instrument unit 4, and configured to advance and retract in opposite directions to each other to configure an input member configured to transmit the driving force in the advance direction upon advance toward the surgical instrument unit 4.

In addition, the pinion 12 is engaged with the first input member 11 and the second input member 13, and configures an inversion interlocking member of drive unit (a second inversion interlocking member) configured to transmit the moving amount of the first input member 11 to the second input member 13 by inverting the moving direction.

As described above, since the inversion interlocking member of drive unit is provided, the first input member 11 and the second input member 13 can be advanced and retracted by the motor 16, which is one driving source, via the rotation-translation transduction unit 15.

In addition, the pinion 42 is engaged with the first transmission member 41 and the second transmission member 43, and configures an inversion interlocking member of surgical instrument unit (a first inversion interlocking member) configured to transmit the moving amount of one of the first transmission member 41 and the second transmission member 43 to the other of the first transmission member 41 and the second transmission member 43 with inverting the moving direction.

As described above, since the inversion interlocking member of surgical instrument unit is provided, the first transmission member 41 can be advanced and retracted by the motor 16, which is one driving source, via the inversion interlocking member of drive unit, the first input member 11 and the second input member 13.

Next, an attachment and detachment action of the medical manipulator 1 will be described.

In the medical manipulator 1, the connecting convex section 28, the engagement hole section 3c, the connecting convex section 27, and the engagement hole section 4e extend parallel to the central axes $O_2$, $O_3$, and $O_4$ of the surgical instrument drive unit 2, the intermediate member 3, the surgical instrument unit 4, which correspond thereto, and directions along the central axes $O_2$, $O_3$, and $O_4$ form attachment and detachment directions, respectively.

In addition, all of the first input member 11, the first intermediate transmission member 26, and the first transmission member 41, and the second input member 13, the second intermediate transmission member 25, and the second transmission member 43 are disposed parallel to the central axes $O_2$, $O_3$, and $O_4$ corresponding thereto.

For this reason, as described above, the surgical instrument drive unit 2, the intermediate member 3, and the surgical instrument unit 4 can be disposed on the same axes as the central axes $O_2$, $O_3$, and $O_4$, and can be connected by being inserted in directions along the respective central axes.

Here, in the above description, as shown in FIG. 15, an example in which the connection is performed in a state in which the end of the first input member 11 and the end of the second input member 13 are aligned with the connecting end surface 2d, the end of the first intermediate transmission member 26 and the end of the second intermediate transmission member 25 are aligned with the connecting end surfaces 3A and 3b, respectively, and the ends of the first transmission members 41 and 43 are aligned with the connecting end surface 4d has been described. However, the ends of the input members, the intermediate transmission members, and the transmission members can be easily connected even in a state in which the ends are advanced and retracted with respect to the respective connecting end surfaces.

As the pair of release buttons 21 protruding to side portions of the surgical instrument unit 4 are respectively pushed thereinto, the surgical instrument unit 4 can be removed from the intermediate member 3. Accordingly, the ends of the respective shaft sections 21b press the engagement arm sections 20A and 20B toward the central axis $O_4$, and locking between the engagement claw section 20b and the locking surface 4g is released. Accordingly, the surgical instrument unit 4 and the intermediate member 3 can be separated from each other in directions along the central axes $O_4$ and $O_3$.

Here, the first transmission member 41 and the first intermediate transmission member 26, and the second transmission member 43 and the second intermediate transmission member 25 merely abut each other in directions along the central axes $O_4$ and $O_3$, respectively. For this reason, even in a state in which the members advance and retract with respect to the connecting end surfaces 4d and 3A, the members can be easily separated from each other.

For this reason, the surgical instrument unit 4 can be removed from the intermediate member 3 by only an action of pushing the release button 21 and separating the surgical instrument drive unit 2 and the intermediate member 3 from each other in the axial direction.

In addition, in the removal action, the intermediate member 3 may be mounted on the surgical instrument drive unit 2, or may be previously removed from the surgical instrument drive unit 2.

Similarly, in order to remove the intermediate member 3 from the surgical instrument drive unit 2, the pair of release buttons 21 protruding to the side portions of the intermediate member 3 are pushed thereinto, respectively. Accordingly, the ends of the respective shaft sections 21b press the engagement arm sections 20A and 20B toward the central axis $O_3$, and locking between the engagement claw section 20b and the locking surface 3g is released. Accordingly, the intermediate member 3 and the surgical instrument drive unit 2 can be separated from each other in direction along the central axes $O_3$ and $O_2$.

Here, the first intermediate transmission member 26 and the first input member 11, and the second intermediate transmission member 25 and the second input member 13 merely abut each other in directions along the central axes $O_3$ and $O_2$, respectively. For this reason, even in a state in which the members advance and retract with respect to the connecting end surfaces 3B and 2d, the members can be easily separated from each other.

For this reason, the intermediate member 3 can be removed from the surgical instrument drive unit 2 by only an action of pushing the release button 21 and separating the intermediate member 3 and the surgical instrument drive unit 2 from each other in the axial direction.

In addition, in the removal action, the intermediate member 3 may be mounted on the surgical instrument unit 4 or may be previously removed from the surgical instrument unit 4.

In addition, when the surgical instrument unit 4 is removed from the surgical instrument drive unit 2, the driving force is not transmitted to the first transmission member 41. However, in the present embodiment, since the manipulation member 44 is provided with the second transmission member 43, the driving force can be transmitted to the first transmission member 41 by manually adjusting a position of the manipulation member 44.

For this reason, even after the surgical instrument unit 4 is removed, an opening/closing state of the forceps section 30 can be easily changed or a curvature of the joint 31 can be easily varied.

In addition, advance and retraction positions of the first transmission member 41 and the second transmission member 43 can be adjusted and can be easily housed to be aligned with the connecting end surface 4d.

As described above, in the medical manipulator 1, the advance and retraction directions of the input member, the intermediate transmission member, and the transmission member are directions parallel to the attachment and detachment direction. For this reason, upon connection, the connection can be performed by merely pushing the members toward each other in the axial direction. In addition, in the case of the removal, the removal can be performed by merely separating the members from each other in the axial direction after the action of pushing the release button 21. For this reason, for example, since the action such as a rotation action does not occur in the insertion or connection, attachment and detachment can be easily and rapidly performed.

As described above, according to the medical manipulator 1 according to the present embodiment, the input members, which constitute pairs, configured to transmit the driving force from the surgical instrument drive unit to the surgical instrument unit and the first and second transmission members are disposed opposite to each other at the ends in the attachment and detachment direction to transmit the driving force, thereby moving only in the attachment and detachment direction, and performing the attachment and detachment. For this reason, the attachment and detachment of the surgical instrument unit on the surgical instrument drive unit can be easily and rapidly performed.

(Modified Example)

Next, a medical manipulator according to a modified example of the present embodiment will be described.

Figure 17:
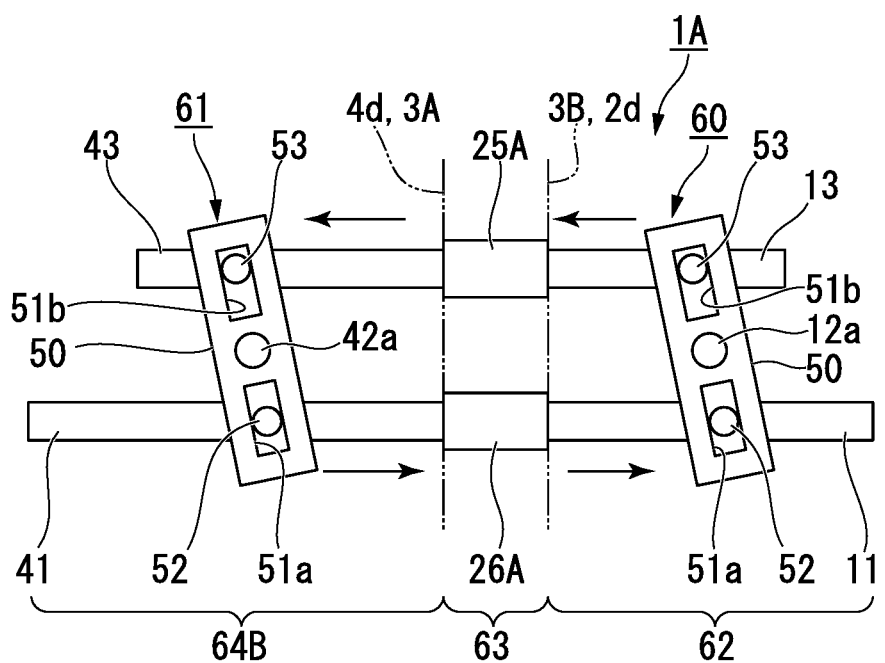
FIG. 17 is a schematic view showing a configuration of major parts of a medical manipulator according to a modified example of the first embodiment of the present invention.

FIG. 17 is a schematic view showing a configuration of major parts of the medical manipulator according to the modified example of the first embodiment of the present invention.

As shown in FIG. 17, a medical manipulator 1A according to the modified example includes a surgical instrument drive unit 62, an intermediate member 63, and a driving force transmission section 64B, instead of the surgical instrument drive unit 2, the intermediate member 3, and the driving force transmission section 4B according to the first embodiment.

Hereinafter, the modified example will be described focusing on different points from the first embodiment.

The surgical instrument drive unit 62 includes a reciprocation drive unit 60 as shown in FIG. 17, instead of the reciprocation drive unit 10 according to the first embodiment.

The reciprocation drive unit 60 does not include the sliding block 12b and the coil spring 18 of the reciprocation drive unit 10. In addition, the reciprocation drive unit 60 includes a cam link 50 (an inversion interlocking member of drive unit, a second inversion interlocking member), instead of the pinion 12.

The cam link 50 is a rectangular plate-shaped member having a center portion turnably supported by the rotary shaft 12a. Cam holes 51a and 51b having a long hole shape are provided on an axis passing through a center of the rotary shaft 12a. The cam link 50 overlaps and intersects the first input member 11 and the second input member 13, and is disposed such that the cam hole 51a overlaps the first input member 11 and the cam hole 51b overlaps the second input member 13.

An engagement pin 52 engaged with the cam hole 51a and movable along the cam hole 51a protrudes upward from the first input member 11. In addition, an engagement pin 53 engaged with the cam hole 51b and movable along the cam hole 51b protrudes upward from the second input member 13.

Further, the first input member 11 and the second input member 13 of the reciprocation drive unit 60 and a first transmission member 41 and a second transmission member 43 of a reciprocation drive unit 61 are constituted by a metal material formed of a ferromagnetic material.

The intermediate member 63 includes a first intermediate transmission member 26A and a second intermediate transmission member 25A having the same shape as the first intermediate transmission member 26 and the second intermediate transmission member 25 and formed of a permanent magnet or a metal member, at least a distal end portion and a proximal end portion of which are magnetized, instead of the first intermediate transmission member 26 and the second intermediate transmission member 25 of the intermediate member 3 according to the first embodiment.

The driving force transmission section 64B includes the reciprocation drive unit 61, instead of the reciprocation drive unit 40 according to the first embodiment.

The reciprocation drive unit 61 does not include the sliding block 42b and the coil spring 18 of the reciprocation drive unit 40. In addition, the reciprocation drive unit 61 includes the cam link 50 having the same shape, instead of the pinion 42.

However, the cam link 50 of the reciprocation drive unit 61 overlaps and intersects the first transmission member 41 and the second transmission member 43, and is disposed such that the cam hole 51a overlaps the first transmission member 41 and the cam hole 51b overlaps the second transmission member 43.

In addition, the engagement pin 52 engaged with the cam hole 51a and movable along the cam hole 51a protrudes upward from the first transmission member 41. Further, the engagement pin 53 engaged with the cam hole 51b and movable along the cam hole 51b protrudes upward from the second transmission member 43.

According to the above-mentioned configuration, in the reciprocation drive unit 60 of the medical manipulator 1A, the driving force is transmitted to the cam link 50 from the engagement pin 52 moving with the first input member 11 via the cam hole 51a by the advance and retract action of the first input member 11. Accordingly, the cam link 50 is turned about the rotary shaft 12a, and movement of the cam hole 51a is inverted and transmitted to the cam hole 51b.

For this reason, when the engagement pin 52 is moved to the proximal end side (the distal end side), the engagement pin 53 engaged with the cam hole 51b is moved to the distal end side (the proximal end side) by the same moving amount. Accordingly, since relative movement between the first input member 11 and the second input member 13 is substantially the same as in the reciprocation drive unit 60, the driving force can be transmitted to the intermediate member 63, similar to the reciprocation drive unit 10.

In addition, similarly, the cam link 50 of the reciprocation drive unit 61 also includes a configuration which substitutes the pinion 42 of the reciprocation drive unit 40 according to the first embodiment. For this reason, similar to the reciprocation drive unit 40, the driving force can be transmitted from the intermediate member 3 to the first transmission member 41.

In addition, in the modified example, since both ends of the first intermediate transmission member 26A and both ends of the second intermediate transmission member 25A have magnetic properties, when the first input member 11, the first transmission member 41, the second input member 13, and the second transmission member 43 formed of a ferromagnetic material approach the first intermediate transmission member 26A or the second intermediate transmission member 25A, a magnetic force is applied to pull the members toward each other.

For this reason, in the mutual mounting state, the first input member 11, the first intermediate transmission member 26A, and the first transmission member 41 are integrated as one shaft member, and the second input member 13, the second intermediate transmission member 25A, and the second transmission member 43 are integrated as one shaft member. For this reason, the driving force can be efficiently transmitted.

That is, the same effect as the coil spring 18 according to the first embodiment is provided. Here, the coil spring 18 and the sliding block 12b can be omitted to reduce the number of parts, and the rotary shafts 12a and 42a can be fixed to the surgical instrument drive unit 62 and the surgical instrument unit 4, respectively. For this reason, the configuration can be further simplified. In addition, the size can be further reduced.

The modified example is an example in which the first intermediate transmission members 26A and 26B function as both of a biasing unit of surgical instrument unit and a biasing unit of drive unit by a suction force.

(Second Embodiment)

Next, a medical manipulator according to a second embodiment of the present invention will be described.

Figure 18:
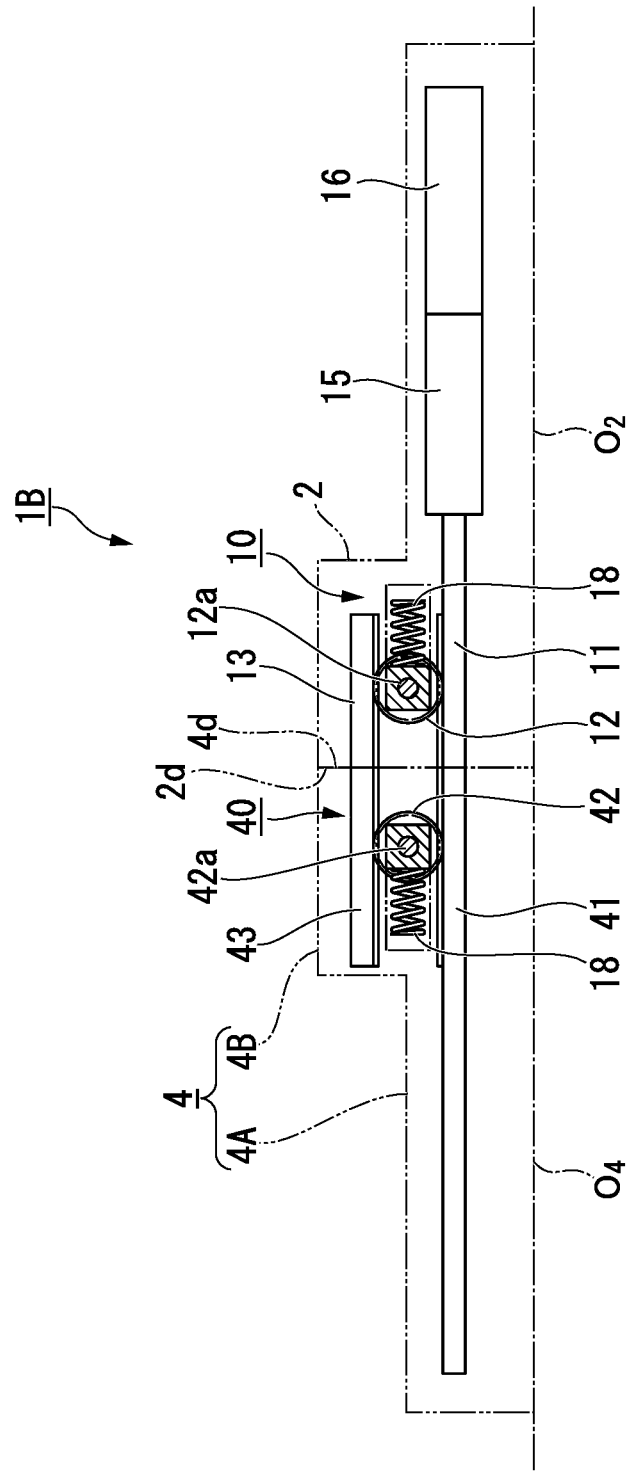
FIG. 18 is a schematic view showing a configuration of major parts of a medical manipulator according to a second embodiment of the present invention.

FIG. 18 is a schematic view of major parts of the medical manipulator according to the second embodiment of the present invention.

In the medical manipulator 1B according to the present embodiment, as the major parts are schematically shown in FIG. 18, the intermediate member 3 can be omitted from the medical manipulator 1 according to the first embodiment, a length of the connecting convex section 28 of the surgical instrument drive unit 2 can be matched to a length of the engagement hole section 3c of the surgical instrument drive unit 2, and the surgical instrument unit 4 can be directly connected to the surgical instrument drive unit 2.

For this reason, in the medical manipulator 1B, the distal end portion of the first input member 11 and the proximal end portion of the first transmission member 41, and the distal end portion of the second input member 13 and the proximal end portion of the second transmission member 43 directly face and abut each other.

According to the above-mentioned configuration, as the intermediate member 3 is merely not provided, substantially similar to the first embodiment, the input members, which constitute pairs, configured to transmit the driving force from the surgical instrument drive unit to the surgical instrument unit and the first and second transmission members are disposed opposite to each other at the ends in the attachment and detachment direction to transmit the driving force, thereby moving in the attachment and detachment direction, and performing the attachment and detachment. For this reason, the attachment and detachment of the surgical instrument unit with respect to the surgical instrument drive unit can be easily and rapidly performed.

In addition, in the above description, the case in which the input members disposed to form a pair at the end of the surgical instrument drive unit 2, configured to advance and retract in opposite directions, and configured to transmit the driving force in an advance direction upon advance toward the surgical instrument unit 4 are constituted by the reciprocation drive units 10 and 60. According to the above-mentioned configuration, since the rotation-translation transduction unit 15 and the motor 16, which are a driving source with respect to the pair of first input member 11 and second input member 13, may be provided in one set, a simple configuration can be obtained.

However, when a disposition space of the driving source has a margin, for example, the pinion 12 and the cam link 50, which constitute an inversion interlocking member of drive unit, may be omitted from the reciprocation drive units 10 and 60, a pair of driving sources configured to independently drive the first input member 11 and the second input member 13 may be provided, a driving amount of the pair of driving sources may be controlled, and the first input member 11 and the second input member 13 may be moved in opposite directions to each other.

In addition, in the above description, the case in which the input members of the surgical instrument drive unit are disposed at one end in the attachment and detachment direction with respect to the surgical instrument unit to form a pair and configured to advance and retract in opposite directions to each other by the same distance, and the driving force is transmitted in the advance direction upon advance toward the surgical instrument unit has been described. However, the moving amounts of the pair of input members may be set to a moving amount corresponding to the moving amounts of the first transmission member and the second transmission member, which are opposite to each other, such that transmission of the driving force is not interfered. For this reason, the moving amounts of the input members may be different from each other, and the advance and retraction by the same distance is not necessary.

For example, in the first embodiment, instead of the pinions 12 and 42, a two-stage pinion in which two pinions having different numbers of teeth are provided on the same shaft may be employed to constitute an inversion mechanism having a speed reduction ratio. In this case, a ratio between the moving amount of the first input member 11 and the first transmission member 41 and the moving amount of the second input member 13 and the second transmission member 43 is correspondingly different from the speed reduction ratio (a ratio of the numbers of teeth). However, since the first input member 11 and the first transmission member 41 are in contact with and interlocked with each other and the second input member 13 and the second transmission member 43 are in contact with and interlocked with each other, the driving force can be transmitted with no trouble.

A force amount input into the first transmission member 41 and a force amount input into the second transmission member 43 can be varied by the inversion mechanism having a speed reduction ratio. For this reason, the speed reduction ratio may be appropriately set in accordance with friction of a transmission system or a force amount desired to be output.

In addition, in the above description, the case in which all of the reciprocation drive units 10, 40, 60, and 61 are provided in four sets has been described. However, the number of provided units can be set to an appropriate number of one or more in accordance with the number of first transmission members required to be connected to the effector.

Further, in the above description, the case in which all of the reciprocation drive units 10, 40, 60, and 61 are provided in four sets and the units are radially disposed with respect to the central axis of the surgical instrument drive unit 2 or the surgical instrument unit 4. However, disposition of the reciprocation drive unit is not limited to the radial shape. For example, the reciprocation drive units may be disposed parallel to one direction or may be disposed plane-symmetrically with respect to one plane of symmetry.

Furthermore, in the above description, the case in which, in the plurality of sets of reciprocation drive units 10 and 60 disposed in a radial shape, the first input member 11 is disposed at a position nearer the central axis than the second input member 13, and in particular, the first input member 11 is aligned with a certain circumference has been described. According to the above-mentioned configuration, since the first input member 11 has a distance from the central axis $O_2$ shorter than that of the second input member 13, a diameter of a circle surrounding the first input member 11 about the central axis $O_2$ is smaller than a diameter of a circle surrounding the second input member 13. Accordingly, disposition positions of the first transmission members 41 opposite to the respective first input members 11 are positioned on a circle equidistant from the central axis $O_4$.

For this reason, in comparison with the case in which the second input member 13 is disposed nearer the central axis $O_2$ than the first input member 11, an outer diameter of the shaft section 32 of the surgical instrument drive unit 2 is reduced to enable configuration of the surgical instrument unit 4 having a small diameter, which can be easily inserted into the body cavity.

In addition, in the above description, the case in which the biasing unit of surgical instrument unit and the biasing unit of drive unit are provided has been described. However, for example, when backlash or the like interferes with manipulation of the surgical instrument unit, any one of them may be provided. In addition, neither of them may be provided.

Further, in the above description, the case in which the width in the circumferential direction of the first intermediate transmission member 26 is the same as that of the first input member 11 and the first transmission member 41, and the width in the circumferential direction of the second intermediate transmission member 25 is the same as that of the second input member 13 and the second transmission member 43 has been described. However, in these examples, sizes and shapes of cross-sections of the first intermediate transmission member 26 and the second intermediate transmission member 25 can be variously changed.

For example, a cross-sectional shape of the first intermediate transmission member 26 can be larger than that of the first input member 11 and the first transmission member 41, and a cross-sectional shape of the second intermediate transmission member 25 can be larger than that of the second input member 13 and the second transmission member 43. In this case, shapes of the distal end portions of the guide grooves 2k and 2j and shapes of the proximal end portions of the guide grooves 4i and 4n expand in a hole shape in which the first intermediate transmission member 26 and the second intermediate transmission member 25 can advance, within a range in which the first intermediate transmission member 26 and the second intermediate transmission member 25 corresponding thereto advance.

As a result, even when a positioning error of the intermediate member 3 upon connection occurs to a certain extent, the connection can be performed with no interference with transmission of the driving force.

In addition, in the above description, the case in which the driving source converts rotation of the motor 16 into translation acting movement by the rotation-translation transduction unit 15 to transmit the translation acting movement to the pair of input members has been described. However, the driving force transmitted to the reciprocation drive unit 10 is not limited to a direct drive. For example, the rotation-translation transduction unit 15 may be omitted, and the motor 16 may directly and rotationally drive the pinion 12 to supply the driving force.

Hereinabove, while preferred embodiments of the present invention have been described, the present invention is not limited to the embodiments. Additions, omissions, substitutions, and other modifications can be made to the present invention without departing from the spirit and scope of the present invention. The present invention is not limited to the above-mentioned description, and is only limited by the appended claims.

What is claimed is:

1. A medical manipulator comprising:
a surgical instrument unit having an effector configured to manipulate a target object; and
a surgical instrument drive unit provided detachably with respect to the surgical instrument unit and configured to supply a driving force for driving the effector,
wherein the surgical instrument drive unit comprises:
first and second rods disposed at one end of the surgical instrument drive unit in an attachment and detachment direction to the surgical instrument unit and configured to advance and retract in opposite directions to each other, and configured to transmit the driving force in an advance direction upon advance toward the surgical instrument unit; and
an actuator configured to advance and retract the first and second rods, and
the surgical instrument unit comprises:
a third rod opposite to one of the first and second rods and supported so as to advance and retract in one end of the surgical instrument unit in the attachment and detachment direction to the surgical instrument drive unit, configured to receive the driving force by the one of the first and second rods and move in the same direction as the one of the first and second rods, and connected to the effector in the other end of the surgical instrument unit in the attachment and detachment direction;
a fourth rod opposite to the other of the first and second rods and supported so as to advance and retract in the one end of the surgical instrument unit in the attachment and detachment direction to the surgical instrument drive unit, and configured to receive the driving force by the other of the first and second rods and move in the same direction as the other of the first and second rods; and
a first mechanism engaged with the third rod and the fourth rod, and configured to transmit a moving amount of one of the third rod and the fourth rod to the other of the third rod and the fourth rod while inverting a moving direction.

2. The medical manipulator according to claim 1, wherein the first and second rods, the third rod, the fourth rod, and the first mechanism are provided in a plurality of sets, and in each of the plurality of sets, the one of the first and second rods is disposed closer to a center of an end of the surgical instrument drive unit in the attachment and detachment direction than the other of the first and second rods.

3. The medical manipulator according to claim 1, further comprising an intermediate member provided between the surgical instrument unit and the surgical instrument drive unit and detachably connected to the surgical instrument unit and the surgical instrument drive unit, wherein
the intermediate member comprises:
a surgical instrument unit side end detachably connected to the one end of the surgical instrument unit;
a drive unit side end detachably connected to the one end of the surgical instrument drive unit;
a first intermediate rod opposite to and abutting the third rod and the one of the first and second rods;
a second intermediate rod opposite to and abutting the fourth rod and the other of the first and second rods;
a first guide hole into which the third rod, the one of the first and second rods, and the first intermediate rod are inserted so as to advance and retract, the first guide hole being configured to guide the first intermediate rod so as to advance and retract; and
a second guide hole into which the fourth rod, the other of the first and second rods, and the second intermediate rod are inserted so as to advance and retract, the second guide hole being configured to guide the second intermediate rod so as to advance and retract.

4. The medical manipulator according to claim 1, wherein the fourth rod comprises a surface movable between an attached position and a detached position corresponding to the attachment and detachment direction of the surgical instrument unit, respectively, the surface protruding from the surgical instrument unit in a direction intersecting the attachment and detachment direction of the surgical instrument unit.

5. The medical manipulator according to claim 1, wherein
the one of the first and second rods is configured to advance and retract by being connected to the actuator, and
the surgical instrument drive unit further comprises a second mechanism provided between the first and second rods, engaged with the first and second rods, and configured to transmit a moving amount of the one of the first and second rods to the other of the first and second rods while inverting the moving direction.

6. The medical manipulator according to claim 5, wherein the surgical instrument drive unit further comprises a spring configured to bias the second mechanism toward the one end of the surgical instrument drive unit in the attachment and detachment direction to the surgical instrument unit.

7. The medical manipulator according to claim 6, wherein the spring is a coil spring.

8. The medical manipulator according to claim 1, wherein the surgical instrument unit further comprises a spring configured to bias the first mechanism toward the one end of the surgical instrument unit in the attachment and detachment direction to the surgical instrument drive unit.

9. The medical manipulator according to claim 8, wherein the spring is a coil spring.

10. A medical manipulator comprising:
a surgical instrument unit having an effector configured to manipulate a target object; and
a surgical instrument drive unit provided detachably with respect to the surgical instrument unit and configured to supply a driving force for driving the effector,
wherein the surgical instrument drive unit comprises:
first and second rods disposed at one end of the surgical instrument drive unit in an attachment and detachment direction to the surgical instrument unit and configured to advance and retract in opposite directions to each other, and configured to transmit a driving force in an advance direction upon advance toward the surgical instrument unit; and
the surgical instrument unit comprises:
a third rod opposite to one of the first and second rods and supported so as to advance and retract in one end of the surgical instrument unit in the attachment and detachment direction to the surgical instrument drive unit, configured to receive the driving force by the one of the first and second rods and move in the same direction as the one of the first and second rods, and connected to the effector in the other end of the surgical instrument unit in the attachment and detachment direction;
a fourth rod opposite to the other of the first and second rods and supported so as to advance and retract in the one end of the surgical instrument unit in the attachment and detachment direction to the surgical instrument drive unit, and configured to receive the driving force by the other of the first and second rods and move in the same direction as the other of the first and second rods; and a mechanism having two or more mechanical components, the mechanism being engaged with the third rod and the fourth rod, and configured to transmit a moving amount of one of the third rod and the fourth rod to the other of the third rod and the fourth rod while inverting a moving direction.

11. The medical manipulator according to claim 10, wherein the two or more mechanical components comprise a rack and a mating pinion.

12. The medical manipulator according to claim 10, wherein the two or more mechanical components comprise a cam and a mating follower.

13. The medical manipulator according to claim 10, further comprising an actuator configured to apply the driving force to advance the first and second rods.

14. The medical manipulator according to claim 13, wherein the actuator is a motor.

15. The medical manipulator according to claim 10, wherein the inversion interlocking member comprises two or more mechanical components.

16. The medical manipulator according to claim 15, wherein the two or more mechanical components comprise a rack and a mating pinion.

17. The medical manipulator according to claim 15, wherein the two or more mechanical components comprise a cam and a mating follower.

18. A medical manipulator comprising:
   a surgical instrument unit having an effector configured to manipulate a target object; and
   a surgical instrument drive unit provided detachably with respect to the surgical instrument unit and configured to supply a driving force for driving the effector,
   wherein the surgical instrument drive unit comprises:
      first and second rods disposed at one end of the surgical instrument drive unit in an attachment and detachment direction to the surgical instrument unit and configured to advance and retract in opposite directions to each other, and configured to transmit a driving force in an advance direction upon advance toward the surgical instrument unit; and
   the surgical instrument unit comprises:
      a third rod opposite to one of the first and second rods and supported so as to advance and retract in one end of the surgical instrument unit in the attachment and detachment direction to the surgical instrument drive unit, configured to receive the driving force by the one of the first and second rods and move in the same direction as the one of the first and second rods, and connected to the effector in the other end of the surgical instrument unit in the attachment and detachment direction;
      a fourth rod opposite to the other of the first and second rods and supported so as to advance and retract in the one end of the surgical instrument unit in the attachment and detachment direction to the surgical instrument drive unit, and configured to receive the driving force by the other of the first and second rods and move in the same direction as the other of the first and second rods; and
      an inversion interlocking member engaged with the third rod and the fourth rod, and configured to transmit a moving amount of one of the third rod and the fourth rod to the other of the third rod and the fourth rod while inverting a moving direction.

19. The medical manipulator according to claim 18, further comprising an actuator configured to apply the driving force to advance the first and second rods.

20. The medical manipulator according to claim 19, wherein the actuator is a motor.

* * * * *